US009801755B2

(12) United States Patent
Summer

(10) Patent No.: US 9,801,755 B2
(45) Date of Patent: Oct. 31, 2017

(54) TONGUE RETAINER

(76) Inventor: John D. Summer, Portland, OR (US)

(*) Notice: Subject to any disclaimer, the term of this patent is extended or adjusted under 35 U.S.C. 154(b) by 710 days.

(21) Appl. No.: 13/310,601

(22) Filed: Dec. 2, 2011

(65) Prior Publication Data

US 2012/0138071 A1 Jun. 7, 2012

Related U.S. Application Data

(60) Provisional application No. 61/458,759, filed on Dec. 2, 2010, provisional application No. 61/459,252, filed on Oct. 10, 2010.

(51) Int. Cl.
*A61F 5/56* (2006.01)

(52) U.S. Cl.
CPC .................................. *A61F 5/566* (2013.01)

(58) Field of Classification Search
USPC ........ 128/845, 848, 859, 860; 433/6, 18, 19, 433/21, 140; D24/180; 600/240; 602/902
See application file for complete search history.

(56) References Cited

U.S. PATENT DOCUMENTS

| | | |
|---|---|---|
| 4,198,967 A | 4/1980 | Dror |
| 4,505,672 A | 3/1985 | Kurz |
| 4,676,240 A | 6/1987 | Gardy |
| 4,884,581 A | 12/1989 | Rescigno |
| 4,969,822 A | 11/1990 | Summer |
| 5,066,226 A | 11/1991 | Summer |
| 5,176,618 A | 1/1993 | Freedman |
| 5,373,859 A | 12/1994 | Forney |
| 5,465,734 A | 11/1995 | Alvarez et al. |
| 5,592,951 A | 1/1997 | Gastagnaro et al. |
| 5,659,540 A | 7/1997 | Alvarez et al. |
| 5,715,840 A | 2/1998 | Hall |
| 5,915,385 A | 6/1999 | Hakimi |

(Continued)

FOREIGN PATENT DOCUMENTS

WO    WO 2006/125216    11/2006

OTHER PUBLICATIONS

International Search Report dated Sep. 28, 2007, issued by the International Searching Authority in corresponding PCT Application No. PCT/US06/019759, filed May 18, 2006.

(Continued)

*Primary Examiner* — Caitlin Carreiro
(74) *Attorney, Agent, or Firm* — Klarquist Sparkman, LLP

(57) ABSTRACT

A tongue grasping and restraining device holds the tongue securely during sleep in order to minimize the risk of the tongue slipping back and blocking the throat. Plural tongue gripping projections are coupled to upper and lower supports. One or more of the upper and lower supports are biased together into a tongue engaging position. A tongue depressor can extend rearwardly and downwardly from the upper support to depress the user's tongue to further open the user's airway. The position of the tongue depressor can be adjustable. The upper support is coupled to the user's upper jaw, for example, to a denture, dental appliance or other form of an upper jaw coupler and can be pivoted thereto. The lower support can be hinged to, fixed to, or otherwise joined to a lower jaw coupler. A tube and rod mechanism can couple the jaw couplers together.

38 Claims, 15 Drawing Sheets

(56) References Cited

U.S. PATENT DOCUMENTS

| | | | |
|---|---|---|---|
| 5,964,588 A * | 10/1999 | Cleary | A61C 7/36 |
| | | | 433/18 |
| 6,109,265 A * | 8/2000 | Frantz et al. | 128/848 |
| 6,241,521 B1 | 6/2001 | Garrison | |
| 6,837,246 B1 | 1/2005 | DeLuke | |
| 6,955,172 B2 | 10/2005 | Nelson et al. | |
| 7,451,767 B2 * | 11/2008 | Keropian | A61F 5/566 |
| | | | 128/848 |
| 2003/0190575 A1 * | 10/2003 | Hilliard | A61C 7/00 |
| | | | 433/6 |
| 2008/0188947 A1 | 1/2008 | Sanders | |
| 2009/0126742 A1 * | 5/2009 | Summer | A61F 5/566 |
| | | | 128/848 |
| 2011/0178439 A1 | 7/2011 | Irwin et al. | |
| 2011/0226264 A1 | 9/2011 | Friedman et al. | |

OTHER PUBLICATIONS

Written Opinion dated Sep. 28, 2007, issued by the International Searching Authority in corresponding PCT Application No. PCT/US06/019759, filed May 18, 2006.

Office action dated Apr. 29, 2010, issued in corresponding U.S. Appl. No. 11/986,044, filed Nov. 17, 2007.

Office action dated May 25, 2011, issued in corresponding U.S. Appl. No. 11/986,044, filed Nov. 17, 2007.

* cited by examiner

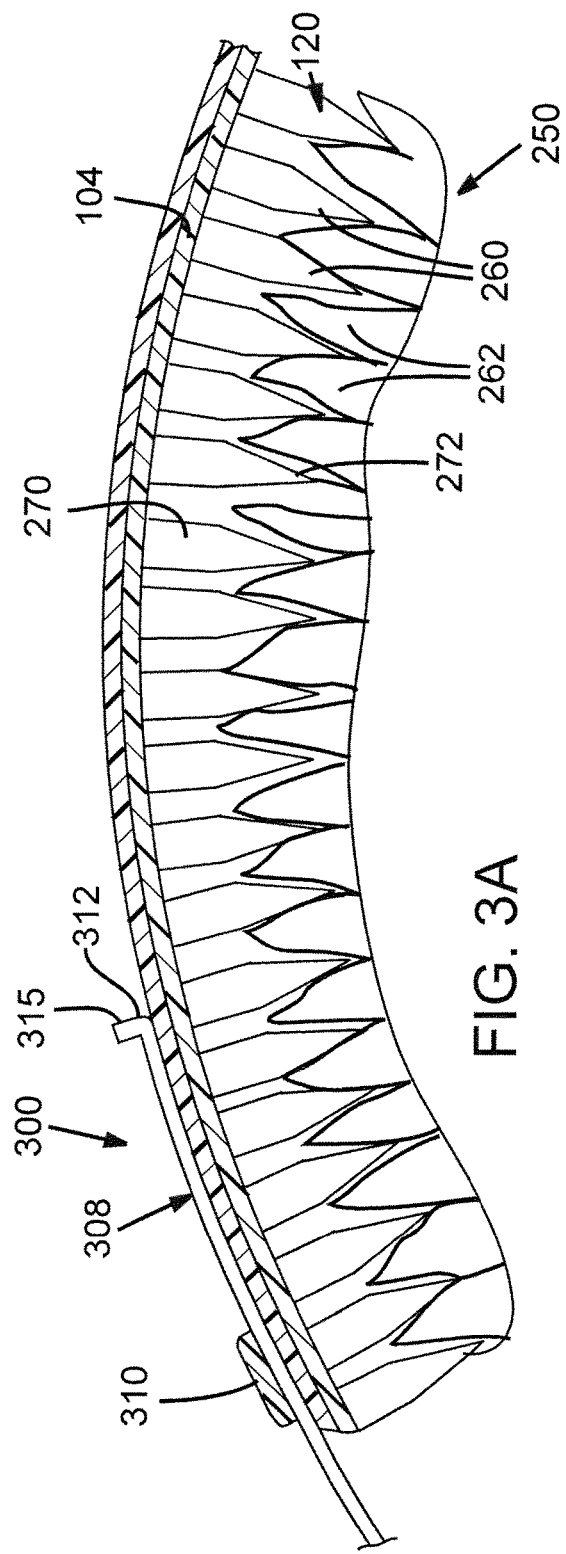
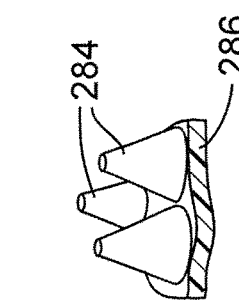
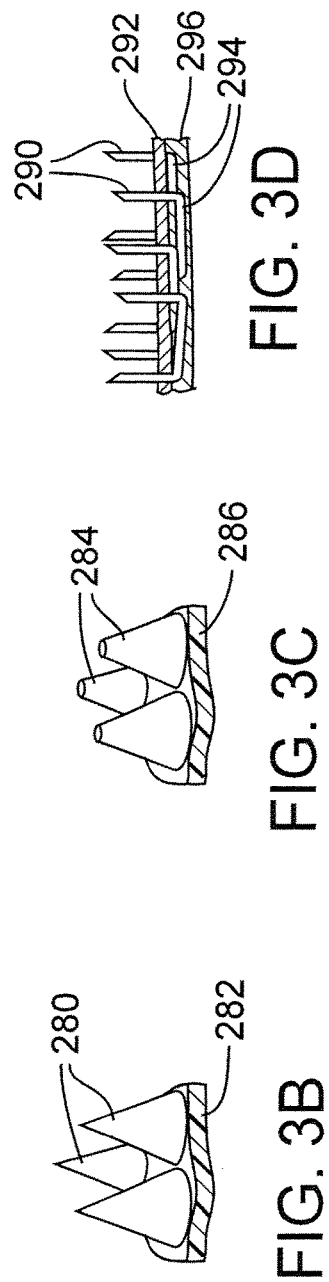
FIG. 3A
FIG. 3B
FIG. 3C
FIG. 3D

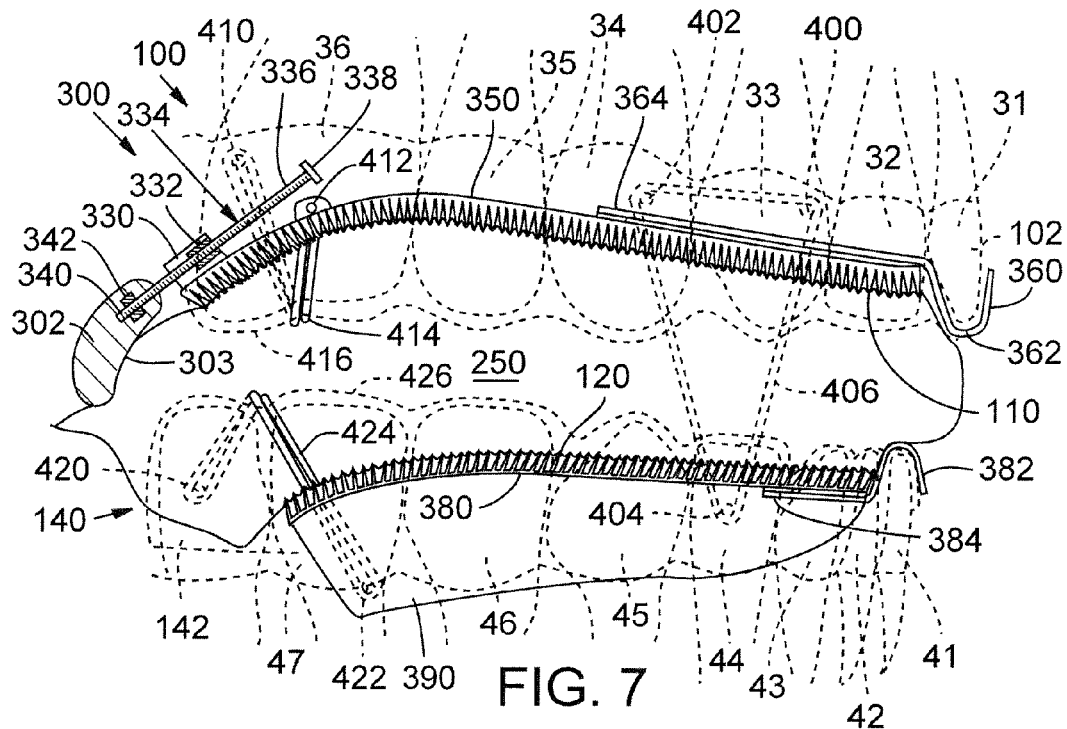

TONGUE RETAINER

CROSS REFERENCE TO RELATED APPLICATIONS

This application claims the benefit of U.S. Provisional Application Ser. No. 61/458,759, filed Dec. 2, 2010, entitled "INTRA-ARCH SOURCE OF BIASING FOR TETHERED TONGUE GRIPPING SURFACES"; and the benefit of U.S. Provisional Application Ser. No. 61/459,252, filed Dec. 10, 2010, entitled "ADJUSTABLE TONGUE REAR DEPRESSOR"; both of which applications are incorporated herein by reference in their entirety.

TECHNICAL FIELD

The technology disclosed herein relates to apparatus for holding an individual's tongue.

BACKGROUND

The prior art describes a number of devices designed to prevent snoring and/or obstructive sleep apnea by holding the lower jawbone forward. Holding the lower jawbone forward creates some additional space in the pharynx, however, generally, obstructive sleep apnea is caused not by lack of pharyngeal space, but by the tongue dropping back and blocking the pharyngeal airway. Holding the lower jaw forward exerts some forward influence on the resting position of the tongue, since the tongue is attached to the lower jawbone. However, the tongue is only loosely attached to lower jawbone, so holding the lower jawbone forward does not necessarily hold the tongue far enough forward to prevent obstructive sleep apnea. Studies have shown that lower jawbone protrusion is a valuable tool in the treatment of obstructive sleep apnea. However, this approach alone would not be effective in many cases.

There is a need for an improved apparatus for opening an individual's airway to reduce the risk of sleep apnea.

SUMMARY

In certain embodiments, an apparatus grasps an individual's tongue by squeezing it from above and/or from above and below between tongue gripping surfaces. The device then restrains the tongue from retrusion by coupling to the upper jaw, such as by engaging the upper teeth. In addition, in certain embodiments, a tongue depressor is positioned to engage the upper surface of a rear portion of the user's tongue to assist in opening the airway. Desirably, the position of the tongue engaging portion of the tongue depressor is adjustable.

The tongue gripping surfaces can be comprised of plural projections, such as a large number of densely arranged points or blades; and more desirably, a multiplicity of closely spaced needle-like projections. The projections, or selected portions thereof, can be supported at a forwardly extending angle toward the tip of the tongue. A biasing force provided by one or more biasing members urges one or more of the tongue gripping surfaces toward one another to grip the tongue. Exemplary biasing members comprise springs or elastic bands. Because of the effectiveness of the tongue gripping surfaces, the tongue retainer can hold the tongue securely all night without compressing the tongue in a manner that causes pain or discomfort. For example, although variable, tongue compression forces of less than from one to two pounds, for example one-half pound or even less can be sufficient to restrain the tongue.

In another exemplary embodiment, the upper tongue gripping surface is carried by an upper support pivotally coupled to an upper jaw coupler, such as comprising a dental appliance, mouthpiece or upper denture and the lower tongue gripping surface is supported by a lower support that is coupled to a lower jaw coupler. The lower support can be fixed or pivotally coupled to the lower jaw coupler. The upper support can be biased downwardly relative to the upper jaw coupler toward the lower support. Biasing elements between the upper and lower jaw couplers can be eliminated. The upper support in one desirable embodiment is pivoted to the upper jaw coupler by a tether extending from a central to rear portion of the upper support to a front portion of the upper jaw coupler. As a result, both the front and rear ends of the upper support and associated upper tongue gripping surface can move upwardly and downwardly to maintain a grip on the user's tongue if the user opens his or her mouth somewhat, such as during sleep. The tongue depressor is desirably also included in this embodiment. Exemplary embodiments can restrain the tongue from retruding beyond its normal resting posture and can be worn comfortably during sleep. Again, these embodiments desirably grasp the tissue of the tongue so effectively that little compressive force is needed to hold the tongue securely for an extended time period, such as all night. Exemplary embodiments are desirably easily openable for insertion or removal of the tongue.

Various embodiments can be comprised of combinations and subcombinations of the following features and aspects.

In accordance with one embodiment, an apparatus for grasping and restraining the tongue of a user comprises: a first upper support; the first upper support comprising an upper support body portion comprising an upper surface, a lower surface, a front, a rear, and first and second sides, the first upper support also comprising a first tongue gripping surface, the first tongue gripping surface comprising a plurality of tongue engaging projections that extend from the lower surface of the upper support body portion toward the upper surface of the front portion of the tongue of a user; an upper jaw coupler adapted to couple the first support to the upper jaw of the user, wherein the upper support body portion is pivotally coupled to the upper jaw coupler such that the entire upper support body portion is movable upwardly and downwardly relative to the upper jaw coupler; a second lower support; the second lower support comprising a lower support body portion comprising an upper surface, a lower surface, a front, a rear, and first and second sides, the second lower support also comprising a second tongue gripping surface, the second tongue gripping surface comprising a plurality of tongue engaging projections that extend from the upper surface of the lower support body portion toward the lower surface of the front portion of the tongue of a user; a lower jaw coupler adapted to couple the second support to the lower jaw of the user; and at least one biasing member coupled to at least one of the first and second supports and adapted to urge at least one of the first and second tongue gripping surfaces toward the other of the first and second tongue gripping surfaces with a front portion of a user's tongue positioned therebetween so as to grasp and restrain the tongue of the user. Telescoping mechanisms can be positioned to extend between jaw couplers at the sides of the jaw couplers to shift the user's lower jaw forwardly relative to the upper jaw.

In accordance with an embodiment, the second lower support can be fixed to the lower jaw coupler. In an alternative embodiment, the second lower support body portion is pivotally coupled to the lower jaw coupler such that the lower support body portion is movable upwardly and downwardly relative to the lower jaw coupler.

As an aspect of an embodiment, a tether can pivotally connect the upper support body portion to the front of the upper jaw coupler. The tether can be connected to the first upper support at a location intermediate to the front and rear of the upper support body portion. In accordance with an embodiment, the tether can be connected to the upper surface of the upper support body portion at a location that is at or rearwardly of the center of the upper support body portion. The tether can be adjustable in length. In one embodiment, a motor can be coupled to the tether, the motor being operable to coil or uncoil the tether to adjust the length of the tether. In addition, in an embodiment, a second tether can pivotally connect the front of the lower support body portion to the lower jaw coupler. Both of the first and second tethers can be adjustable in length.

The at least one biasing mechanism can be coupled to the upper jaw coupler and to the upper surface of the upper support body portion so as to urge the first upper support downwardly toward the second lower support at least when the user's mouth is closed.

In an embodiment, the upper jaw coupler can comprise first and second side portions each with a buccal side and a lingual side and with a downwardly facing upper coupler biting surface. A biasing member engaging projection can extend upwardly from the upper support body portion. The at least one biasing member can extend from a rear portion of the buccal side of the first side portion of the upper jaw coupler, across the biting surface of the first side of the upper jaw coupler, to the biasing engaging projection, across the biting surface of the second side of the upper jaw coupler and to a rear portion of the buccal side of the second side portion of upper jaw coupler, whereby the at least one biasing member exerts a downward force on the upper support portion at least when the user's mouth is in a closed position.

In accordance with another aspect of an embodiment, a biasing member engaging projection can comprise at least one elongated projection extending from a front portion of the upper support toward a rear portion of the upper support. In addition, the at least one biasing member can engage the elongated projection at an upper front portion and an upper rear portion of the elongated projection. The elongated projection can comprise at least one plate. In addition, in one form the at least one plate can comprise a front portion with a first upwardly opening slot having a first band receiving opening and a rear portion with a second upwardly opening slot having a second band receiving opening. Also, the biasing member can comprise at least one elastic band positioned in the first slot and at least one elastic band positioned in the second slot. This biasing member can comprise a single elastic band.

The tongue retainer desirably comprises a tongue depressor coupled to the upper support body portion and projecting rearwardly and downwardly from the upper support body portion for engaging an upper surface of the rear portion of the user's tongue. The tongue depressor is desirably movable relative to the upper support body portion in front to rear directions, rear to front directions, and upward and downward directions. The tongue depressor can be slidably coupled to the upper support body portion. In this regard, the tongue depressor can comprise at least one elongated arm with a first arm portion slidably coupled to the upper support body portion and a second distal arm end portion spaced from the upper support body portion. An enlarged tongue engager can be mounted to the second distal arm end portion. The enlarged tongue engager can be of a desirable shape, such as first and second hemispherical elements positioned such that the rounded surfaces thereof engage the user's tongue. The arm can comprise a bendable material, wherein bending the arm downwardly relative to the upper support body portion shifts the tongue engager downwardly and bending the arm upwardly relative to the upper support body portion shifts the tongue engager upwardly.

As an alternative embodiment, the tongue depressor can comprise at least one elongated arm threadedly coupled to the upper support body portion and extending in a front to rear direction. The arm can comprise a distal end portion spaced from the upper support body portion. An enlarged tongue engager is mounted to the distal end portion of the arm. In this embodiment, rotation of the arm in a first direction shifts the arm and tongue engager axially relative to the upper support body portion in a rearward direction and rotation of the arm in a second direction opposite to the first direction shifts the arm and tongue engager axially relative to the upper support body portion in a forward direction. In addition, as a feature of an embodiment, an arm support can be operatively coupled to the upper surface of the upper body portion for raising and lowering relative to the upper surface of the upper body portion. A first portion of the arm can be carried by the arm support. A pivot can be mounted to the upper support body portion at a location spaced rearwardly of the arm support. The pivot can pivotally couple the arm to the upper support body portion. In this embodiment, raising of the arm support relative to the upper support body portion raises the first portion of the arm and pivots the distal end of the arm and the tongue engager downwardly about the pivot and lowering the arm support relative to the upper support body portion lowers the first portion of the arm and pivots the distal end of the arm and the tongue engager upwardly about the pivot.

These and other features of embodiments disclosed herein will become more apparent from the description below and the accompanying drawings. The disclosure is directed to all novel and non-obvious features and method as disclosed herein alone and in various combinations and sub-combinations as set forth in the claims below. There is no requirement that specific or all advantages set forth herein need to be addressed in any one embodiment. The embodiment disclosed herein are exemplary and do not limit the scope of this disclosure.

DESCRIPTION OF DRAWINGS

FIG. 3A shows an example of filiform papillae of a user's tongue in the process of engagement by projections of one form of an upper tongue gripping surface.

FIGS. 3B, 3C and 3D illustrate exemplary tongue gripping surfaces.

FIG. 7 illustrates a form of tongue retainer with an upper tongue gripping surface support pivotally coupled to an upper jaw coupler and a lower tongue gripping support pivotally coupled to a lower jaw coupler and also showing an alternative faun of tongue depressor.

FIG. 8 is a view of a tongue retainer similar to FIG. 7 with the tongue depressor shown in a more rearward position (in comparison to the position shown in FIG. 7) relative to the upper tongue gripping surface support.

DETAILED DESCRIPTION OF EXEMPLARY EMBODIMENTS

A number of exemplary embodiments of tongue grasping and restraining devices are described below. The examples can be custom devices, which are typically made in a dental laboratory to fit the upper teeth or edentulous ridge as well as the lower teeth. In users who lack upper teeth, an upper denture plate can be used as an upper jaw coupling mechanism.

In this disclosure, the terms "a", "an", and "at least one" means both the singular and the plural. Thus, if two of a particular element are present, there is also a, an, and at least one of these elements that is present. In addition, the term "coupled" means both direct connections between elements and indirect connections of elements through one or more other elements. Also, a component is "embedded" in another component if at least a portion of the component is inserted into the other component. Also, the term "plural" encompasses two or more and the term "multiple" means many (e.g. at least one hundred).

Figure 1:
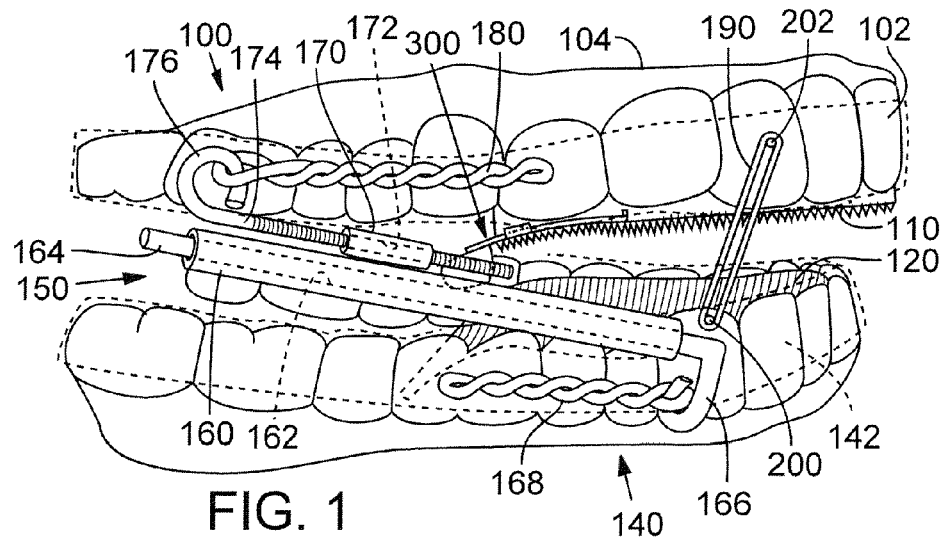
FIG. 1 is a side elevational view of one embodiment of a tongue retainer with one form of a tongue depressor.
Figure 2:
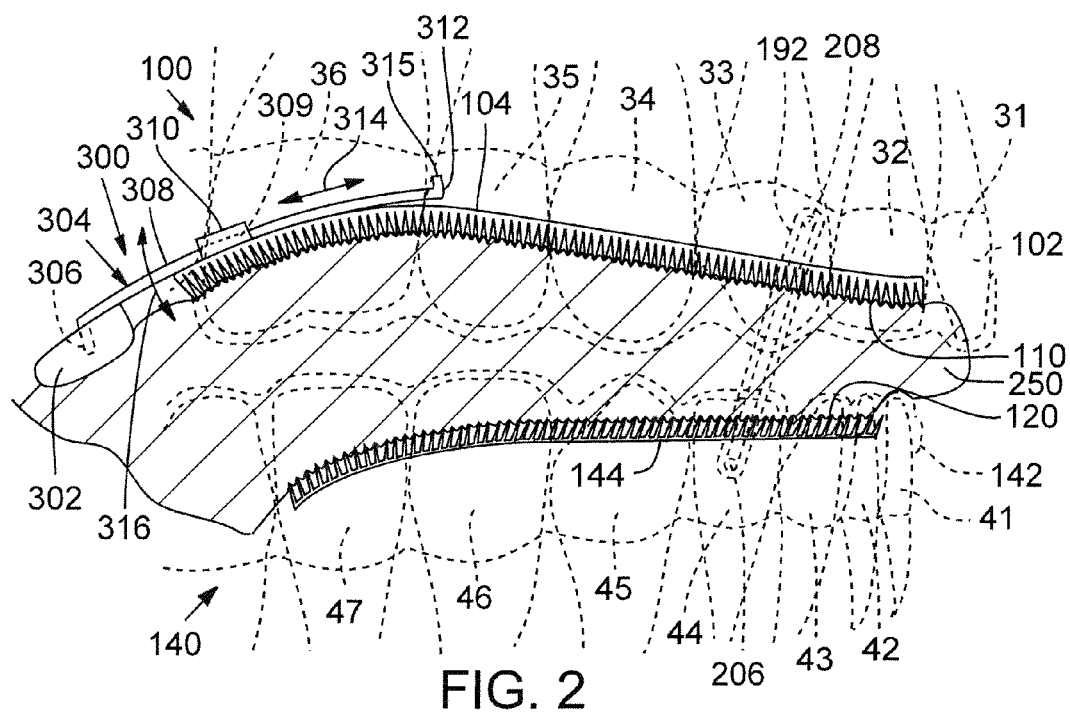
FIG. 2 is a vertical sectional side-view through a portion of the embodiment of FIG. 1 positioned in a user's mouth.
Figure 3:
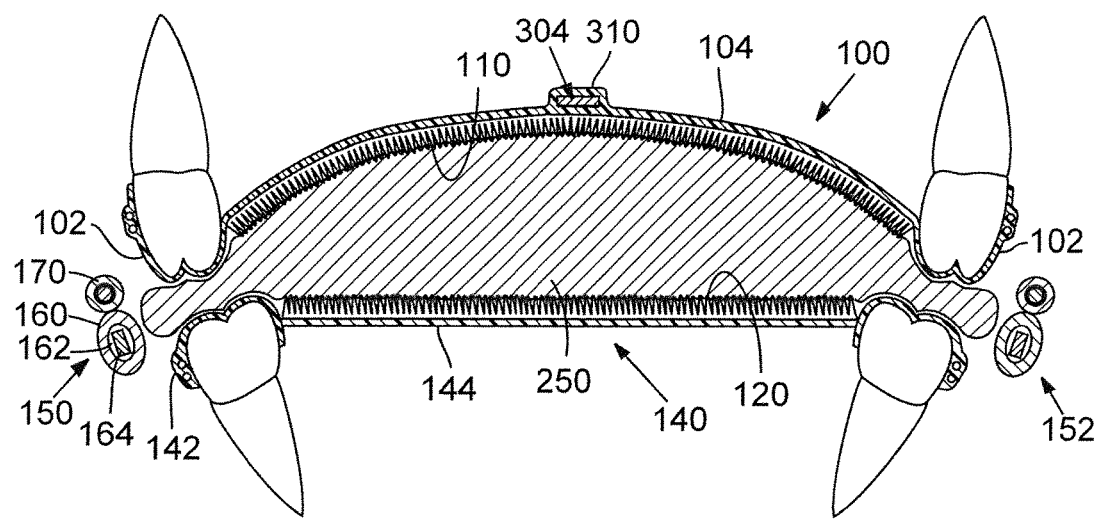
FIG. 3 is a transverse cross sectional frontal view of the embodiment of FIG. 1 positioned in a user's mouth.

An exemplary lower jaw protrusion embodiment as shown in FIGS. 1-3 is one embodiment that typically would be made by a dentist for a person with a full or nearly full dentition.

With reference to FIGS. 1-3, one form of an upper jaw coupler 100 is shown in the form of a dental appliance or mouthpiece having teeth receiving portions 102 for receiving the teeth of the user. The term "jaw coupler" (upper and lower) comprises a dental appliance or device that fits on or over, and/or otherwise engages, a user's teeth or the user's edentulous ridge after the teeth are removed. These devices can comprise, for example, a mouth piece, denture, and material anchored to a user's teeth. A cross-piece, plate or palate portion 104 is joined to the teeth receiving portion and comprises one form of an upper tongue gripping surface support. Other forms of upper support are movable relative to the jaw coupler, such as pivotally coupled to the jaw coupler as explained below. An upper tongue gripping surface 110, in this example, is affixed to support 104 of appliance 100. In this example, the appliance 100 is designed to cover a portion of a user's upper teeth, including at least some teeth along both of the respective sides of the user's mouth. One form of a tongue depressor 300 is also shown in FIG. 1. The illustrated tongue depressor is operable to engage the upper or dorsal surface of a user's tongue to push and hold the tongue away from the user's airway. This and other examples of tongue depressor embodiments will be explained more fully below.

Also, in this example (FIGS. 1-3) a lower jaw coupler 140 is shown. The coupler 140 is shown in the form of a dental appliance or mouthpiece having teeth receiving portions 142 and a cross-piece, lingual plate or portion 144. In this example, the dental appliance 140 is designed to cover a portion of the user's lower teeth, including at least some teeth along both of the respective sides of a lower jaw. In operation, the lower dental appliance 140 can be held, along with the entire lower jaw bone of a user when teeth are received therein, in a protruded position, such as by respective telescopic mechanisms positioned along the respective sides of the apparatus. One specific example of such telescopic mechanisms comprises first and second tube and rod mechanisms (one being indicated at 150 in FIG. 1) along the sides of the teeth receiving portions of the jaw coupling appliances. FIG. 3 illustrates a portion of a second such tube and rod mechanism 152.

A lingual portion 144 of the lower jaw coupler, can support a tongue gripping surface 120 and can be affixed to the lower jaw coupler 140. One advantage of attaching the tongue gripping surfaces to a dental appliance, such as jaw couplers 100, 140, is that appliances that cover the teeth, or at least a majority of such teeth, prevent unwanted tooth movement in response to the forces generated by holding the lower jaw bone forward. Dental appliances are usually able to distribute forces evenly the along the teeth they cover. Appliances that cover the teeth of both upper and lower dental arches prevent adverse movement of all the teeth while also being able to hold the lower jaw bone forward relative to the upper jaw by means such as telescoping tube and rod mechanisms and/or by interlocking inclines.

In the FIGS. 1-3 embodiment, the lower jaw is held in protrusion by two tube and rod telescopic mechanisms 150, 152. With reference to FIG. 1, one of such tube and rod mechanisms 150 will be described. The mechanism comprises a first sleeve 160 that is elongated and defines a longitudinally extending bore 162 therethrough. A rod 164 is slidably received within bore 162. An end portion 166 adjacent to lower appliance 140, and near the forward end of the appliance, can comprise a hook that engages a loop of an anchor 168 embedded within the appliance. A second sleeve 170 is mounted to sleeve 160, such as by welding, and can be stacked above the first sleeve. Sleeve 170 has a longitudinally extending bore 172 that is desirably threaded. A coupler 174 has an externally threaded shank portion that is threadedly received by the sleeve 170. Coupler 174 can be shaped to form a hook 176 at one end thereof. Hook 176 can engage a loop portion of an anchor 180 embedded in appliance 100. With sleeve 160 disconnected from rod 164, the tubing assembly including sleeves 160, 170 can be rotated in a first direction to shift hook 176 away from sleeve 170 to telescopingly lengthen the tube and rod mechanism. In contrast, rotation of the tubing assembly including sleeves 160, 170 in the opposite direction shifts hook 176 toward sleeve 170 and shortens the length of the tube and rod mechanism. Although this construction is advantageous, other telescoping mechanisms, such as other forms of tube and rod mechanisms can also be used.

With reference to FIG. 3, the illustrated rod 164 desirably can have at least one anti-rotation surface, and in FIG. 3 the rod is rectangular in cross-section and thus has four such surfaces. In addition, the bore 162 also can have at least one anti-rotation surface, for example surfaces formed by the generally oval cross-sectional shape of the interior of the bore 162. Consequently, the interior of the bore surfaces engage flat surfaces of the rod and restrict the rod 164 against rotation relative to the sleeve 160. Thus, anti-rotational cooperating surfaces are provided in this tube and rod instruction. The tube and rod mechanisms couple the upper dental appliance 100 to the lower dental appliance 140 in a manner that allows extensions/contraction of the appliances relative to one another. In this example, the anchors 168, 180 can be embedded in acrylic on the outer (buccal) portions of the teeth receiving components of the appliances. When the upper and lower components of the tube and rod mechanisms are engaged in the user's mouth, the rod 164 projects through open ends of the sleeve 160 so as to permit telescopic reciprocation of the rod within the sleeve. As the user's mouth closes, the rod slides into the sleeve until the forward most open end of the sleeve abuts the hook 166 and halts the inward movement of the rod within the sleeve. This thereby halts the retrusive movement of the lower jaw bone relative to the upper jaw.

One or more biasing mechanisms can be provided for biasing at least one of the upper and lower dental appliances 100, 140 toward the other or for biasing at least one of the upper or lower tongue gripping surface supports toward the other. For example, elastic bands, such as rubber bands 190, 192 can engage and be stretched between biasing member coupling extensions. Thus, for example, lower lingual buttons 200, 206 can project outwardly at opposed locations from an outer surface of appliance 140 with such buttons 200, 206 being positioned toward the front of the user's mouth. Similarly, lingual buttons 202, 208 can project outwardly from appliance 100 in opposed directions with such buttons 202, 208 being located toward the front of user's mouth such as slightly forwardly of buttons 200, 206 in this example. Elastic bands 190, 192, extend between respective pairs of the lingual buttons (e.g., band 190 extends between buttons 200, 202 and band 192 extends between buttons 206, 208). Lingual buttons are commonly used in orthodontics for attaching rubber bands. Other mechanisms can alternatively be used to attach biasing members, such as rubber bands or other biasing members, to upper and lower dental appliances. Examples comprise lingual cleats, loops of wire, and structural or anchoring components that are part of a dental appliance. The attachment mechanisms can be located on the outer aspects of the appliances to allow the tongue to fit comfortably between the rubber bands or other biasing mechanisms when they are stretched taut. Plural rubber bands can be used as exemplary biasing mechanisms on each side of the appliances. Orthodontic elastic bands have been found particularly useful. As a specific example, four two ounce (light) force ⅛ inch long latex elastic bands from Dexta Corporation of Napa, Calif. have been found to apply sufficient biasing force to urge the tongue gripping surfaces 110, 120 together for holding the tongue securely without causing pain or ischemia. In other examples described below, one or both the upper and lower gripping surface supports can be biased toward the other support without biasing mechanisms, such as bands, that interconnect the upper and lower jaw couplers.

In the lower jaw protrusion embodiment of FIGS. 1-3, the tongue gripping surfaces 110, 120 are separated for insertion or removal of the tongue simply by opening the user's mouth. This makes insertion and removal of the tongue easy, but does not preclude the possibility of the user's mouth opening and allowing the tongue to slip out of the space between the tongue gripping surfaces when the user is asleep.

The tongue gripping surfaces 110, 120 can be equipped with various mechanisms for frictionally engaging and grasping the user's tongue therebetween. The tongue gripping mechanisms desirably comprise a plurality of projections and most desirably include a multiplicity of such projections. The projections of tongue gripping surface 110 can be different from, identical to, or similar in part to, the projections of tongue gripping surface 120. Also, combinations of different types of projections can be used on either or both of the tongue gripping surfaces 110, 120.

With reference again to FIGS. 1-3, the downward or tongue facing portion of upper tongue gripping surface 110 is desirably comprised of a large number of projections. These projections can be needle-like and can be configured to fit between the filiform papillae which occupy most of the upper (dorsal) surface of the front half of the tongue. These needles can be of any suitable material, such as of plastic or metal, with acrylic and stainless steel being specific examples. FIG. 2 illustrates projections of tongue gripping surface 110 bearing against the upper surface of the user's tongue 250 and projections of the gripping surface 120 bearing against the under surface of the tongue. FIG. 3A illustrates exemplary needle-like projections, some being numbered as 260, shown being positioned between filiform papillae 262 of the user's tongue as the tongue gripping surface 120 engages the upper surface of the tongue.

The projections can take many forms, in one specific example, like the filiform papillae, the needles can be about 0.1 inch long and about 0.03 inch in diameter at their bases. With such small diameters, two or three thousand of the needles can fit on a surface the size of upper tongue gripping surface 120. Desirably, the density of such projections is at least about 500 per inch. Although the ends of the individual needles can be very sharp, the large number of such needles provides a "bed of nails" effect that makes them safe to apply to the tissue of the upper surface of the tongue without the danger of cutting the tissue. In FIG. 3A, the projections each comprise a right cylindrical base portion 270 and a tapered conical needle-like tip portion 272. In the embodiment of FIG. 3B, the projections comprise conical projections 280 projecting from a base 282. In FIG. 3C, the projections comprise frustoconical projections 284 projecting from a base 286. In FIG. 3D, the projections comprise a plurality of staples, two of which are numbered as 290 in FIG. 3D. The staples of this example extend upwardly through a flexible base 292, such as a fabric with the crowns 294 (shown for two of such staples) being embedded in material, such as acrylic 296, coating and impregnating the fabric 292. Additional acrylic can be placed above the fabric as well. The construction of FIG. 3D can be affixed to, for example, the support 104 of the appliance 100. Other examples of suitable projections are described below. Although the densely packed needle-like projections are desirable, the embodiments are not limited to the specific types or shapes of projections described herein.

FIG. 3 illustrates a cross-section, in a transverse plane through the lower jaw protrusion embodiment. As can be seen in FIG. 3, at least a portion of the tongue gripping surface 110 in this embodiment is concave so that the tongue gripping surface more closely follows the curved curvature of the upper surface of the tongue 250. In the embodiment of FIG. 3, the lower tongue gripping surface 120 is shown as being straight in transverse cross-section. However, this surface can similarly be concave at least in part to more closely fit the contour of the undersurface of the user's tongue. With reference to FIG. 2, at least a portion of the upper tongue gripping surface 110 can also be concave in a front to back direction to again closely follow the contour of the user's tongue. In addition, a portion of the lower gripping surface 120 can also be curved, for example concave, in a front to rear direction to more closely fit the lower surface of the user's tongue. It should be noted that these curvatures are not required but do assist in providing a greater surface area of the tongue gripping surfaces in contact with the tongue to thereby enhance the retention of the tongue between the tongue gripping surfaces. Thus, in this exemplary form, the projections forming the upper tongue gripping surface generally follow the same curve as the top of the tongue or the underside of the hard palate of the user. Desirably, the upper tongue gripping surface shown in FIG. 3 extends laterally to fill the area bounded by the upper teeth and rearwardly back to roughly the location of the first molar of the user's mouth. It is to be understood that the tongue gripping surface 110 can also extend laterally onto and over the biting surfaces of some of the teeth.

The projections of the upper and lower tongue gripping surfaces, or at least a plurality of such projections, can be angled forwardly to assist in tongue retention.

As alternatives, the tongue gripping surfaces can comprise numerous rows of blade-like projections, which can be skewed from one another, parallel to one another, and some of such blades desirably can extend in a transverse direction across the user's tongue. Desirably, although not required, the edges of the blades can be angled toward the tip of the tongue as they emerge from their supporting base so that the tongue cannot easily move backward from engagement in the space between the upper and lower tongue gripping surfaces. The upper projections and lower blades can, for example, project toward the tongue tip at a desirable angle. A specific example of a projection angle is an angle of from about 45 degrees to 85 degrees, with a 75 degree angle being a more specific example. The blades can have an edge which is desirably very thin, for example 0.1 inch or less with a specific example being 0.05 inch. The edges of the blades that contact the lower surface of the tongue can also be beveled to create a sharper edge that faces the tip of the tongue.

As a further exemplary manufacturing approach, multiple small areas of a substrate or panel can be partially cut out, leaving a hinge portion coupled to the panel, these cut areas can be pushed out, such as by using a stamping process so as to protrude as multiple projections from the surface of the panel. The projections can be angled toward the tip of the tongue. Yet another approach comprises cutting, or etching, transverse grooves in a substrate or panel to create a textured surface of projecting blades. As a further approach, strips of wire mesh can be cut to leave exposed mesh tips after embedding or fastening the strips to a base. The strips are yet another form of blade or tongue engagement projections. Small serrated blades such as jewelers saw blades mounted in a base have been found to be effective tongue gripping surface elements. Alternatively, plastic blades, such as of acrylic, can be fabricated by making a mold having a surface of saw blades, wetting the mold with acrylic monomer, and then filling the mold with polymer in the same manner as described above in connection with making needle-like projections on a tongue gripping surface. As yet another approach, strips of stainless steel mesh can be cut. The cut side edge of such strips will have projecting mesh wires. The opposite side edge can be embedded or secured to a base to comprise a tongue gripping surface of blades formed of such mesh strips.

As another specific example, numerous parallel densely arranged 0.01 inch thick stainless steel wires projecting downwardly from a base or from the denture can be used. As a specific example, at least several hundred lengths of wire protruding downwardly into the tissue at the top of the tongue from a base affixed to the upper denture 400 can be used. Wires of up to 0.05 inch in diameter can also be used, as well as other cross sectionally dimensioned wires, but larger numbers of smaller diameter wires are more desirable. Such small wires more effectively engage the upper surface of the tongue because they fit between the filiform papillae which occupy most of the tongue upper surface.

In accordance with the example of FIG. 3D, the upper tongue gripping surface 110 can be fabricated to fit the contour of the top of the user's tongue or the downwardly facing surface of the user's palate for an upper denture or other support by first penetrating a flexible support, such as of fabric, with miniature staples and then embedding the fabric or support with the connecting portions (the crowns) of each staple in the acrylic of the denture. The staples can be made of stainless steel wire that is roughly, for example, 0.01 inch in diameter. The legs of the staples can be about 0.12 to 0.2 inches long and the crowns of the staples can be about 0.12 inch long. These dimensions can be varied. Although a specific example of a staple supporting base is fabric, the base can be made of any suitable material such as a poured resin. The base is fixed or mounted to the downwardly facing surface of the upper denture or support 400, such as in a dental laboratory by embedding the base and crowns of the staples in dental acrylic.

With reference to FIG. 2, some of the user's upper teeth are shown with numbers 31, 32, 33, 34, 35 and 36. In addition, some of the user's lower teeth are shown with numbers 41, 42, 43, 44, 45, 46 and 47. With reference to FIGS. 1 and 2, it can be seen in this exemplary embodiment that there is a change in the angle of the plane or direction of the lower tongue gripping surface 120 at the location corresponding to teeth 46 and 47. To enhance the grip, the lower tongue gripping surface 120 can follow the natural curve of the underside of the tongue posteriorly down toward the base of the tongue in the user's neck. In FIG. 3, the lower tongue gripping surface 120 is depicted as flat, however it is understood that tongue gripping surface 120 can also have a concavity to fit the natural contour of the underside of the tongue.

A notch can be provided along the rearmost edge of lower tongue gripping surface 120 with the notch being centrally positioned relative to the lower tongue gripping surface support. The notch can be triangular or of other shapes. The notch is provided to accommodate the lingual frenum, a fiberous attachment between the underside of the tongue and the lower jaw bone. Alternatively, the support for the tongue gripping surface 120 can be shortened in the rearward direction to terminate forwardly of the lingual frenum with a notch then not being provided. As yet another alternative, a flexible membrane or other flexible component can be provided at such location to accommodate the lingual frenum.

Various approaches can be used to fabricate the projections of tongue gripping surfaces 110, 120, such as described in U.S. Published application Ser. No. 11/986,044 to Summer, entitled Tongue Grasping and Restraining Apparatus and Method, filed Nov. 17, 2007, which is incorporated herein in its entirety. One exemplary approach for fabricating needle-like projections of the upper tongue gripping surface 110 of the embodiment of FIG. 1 is described as follows. A plurality of mold forming pins, some of which are supported to project upwardly from a mold pin supporting base. Flexible molding material is utilized in this approach to take an impression of the surface formed by the collection of pin points or tips of the supported pins. The pins can be supported parallel to one another and angled in one direction relative to the base (this results in the molding of tongue engaging projection pins angled forwardly toward the tip of the tongue when the mold is used). The base can be a rigid base, such as one made of plaster and wax which holds the pins so that they do not pull out of the base when the fully set molding material is pulled off the collection of pin points. However, the base can also be a flexible base, such as a tightly woven nylon fabric, holding a collection of pins which are tightly enclosed by a surrounding framework, such as by a thick rubber band, so that the pins can freely move up and down relative to each other and thereby the plane of the pin tips can be adjusted to fit any desired surface contour by simply placing the flexible base supporting such pins on a surface with the appropriate contour.

In one approach to manufacturing the mold, a flexible molding material, such as polyvinylsiloxane, is placed or expressed onto and about 1 mm to 3 mm into the surface of the pin points of the supported pins, allowed to set, and removed. A base material, such as fabric cloth, can be placed over the polyvinylsiloxane after it has been expressed onto the pin points to receive some of the molding materials and give the mold tensile strength to facilitate removal of the mold without tearing it.

The resulting mold can then be used to form a tongue gripping surface. For example, the mold can be used to form a tongue gripping surface of acrylic or other plastic. As a specific example, the mold can be thoroughly wetted with acrylic monomer or other plastic solvent or polymerizing agent. A brush can be used to release trapped air bubbles from the mold. A powdered polymer can then be added to the wetted mold until a sufficiently thick mix of polymerized plastic, such as acrylic, is built up within the mold. Thus, a tongue gripping surface resulting from the use of the mold comprises plural needle-like points supported on an acrylic base. Adding polymer to a mold surface that has already been thoroughly wetted with monomer allows the material, such as acrylic, to reach the full depth made by the impression of the pin points in the mold and thereby create tongue gripping points that are almost as sharp as the pins, which can be comprised of steel, used to make the mold. Vibration can also be used to enhance the distribution of the powdered polymer into the monomer in the ends of the pin point mold depressions. A vacuum can be used to assist in removing trapped air bubbles. The pins can be of other shapes at their tips to result in a tongue gripping surface having alternative shapes.

For individuals without upper teeth, a suitable mechanism for attaching the tongue restraining apparatus to the upper jaw can be by means of an upper denture or base plate that maintains a good fit against the palate and edentulous ridge. The lack of upper teeth provides a great deal of clearance space for accommodating biasing mechanisms, such as torsion springs or other hardware in an upper denture or base plate. Also, a well fitting upper denture or base plate provides sufficient anchorage to the upper jaw to resist retrusion of the tongue when the apparatus is in use.

Desirably, the use of upper and lower tongue gripping surfaces provides a frictional engagement of the tongue. No vacuum is required to hold the tongue in place using these devices.

With reference to FIGS. 2, 4, 5 and 6, an embodiment of a tongue rear depressing device is shown. The tongue depressor is coupled to the upper support 104 and projects rearwardly and downwardly from the support toward the upper surface of the tongue to depress the rear portion of the tongue behind the grip of the upper tongue gripping surface 110. Desirably the tongue depressor is movably mounted to the upper support so that it can move in front and rear directions toward and away from the mouth of the user as well as upwardly and downwardly.

While jaw protrusion and tongue protrusion desirably protect the hypopharynx and oropharynx, they are not very effective in protecting the velopharynx where the rear portion of the tongue can drop back and make contact with the soft palate. One approach for protecting the velopharynx against blockage is by depressing the rear portion of the tongue so that it is held down and away from the soft palate.

Desirably, for effective treatment of obstructive sleep apnea, the entire pharyngeal airway must be kept open for airway passage by protection against obstruction by soft tissues. One critical area of the airway passage is the area between the rear of the tongue (generally the portion between the vallate papillae and the root of the tongue in the area of the hypopharynx) and the soft palate. Opening of the airway passage is assisted by depressing the rear portion of the tongue so that it is held down and away from the soft palate. The illustrated exemplary tongue depressor is provided for this purpose. That is, adding a rearward extension to the upper tongue gripping surface of a tongue retaining apparatus provides a dual functioning tongue retainer, namely retaining the tongue forwardly out of the airway and also assisting in opening the airway by depressing the rear of the tongue.

It is particularly desirable to provide a tongue depressor that is adjustable in anteriorly/posteriorly (front to back) directions as well as upwardly and downwardly so that the furthest downward and backward location of the tongue rear depressor that can be tolerated by the user can more readily be located. This increases the effectiveness of tongue rear depression. Thus, a tongue rear depressor that can be easily adjusted for titrating the tongue rear depression location is desirable. If the tongue depressing portion is located a little too low on the user's tongue, it can irritate the tongue. If the tongue depressing portion is located too high, it is likely to be ineffective. By providing a tongue depressor with adjustable location, it is more effective to locate the tongue depressor where it is most effective without gagging the user or becoming intolerable.

In the embodiment of FIG. 2, the illustrated tongue depressor desirably comprises a smooth tongue contacting surface of a tongue depressor portion 302. The tongue depressor portion is positioned to engage a portion of the upper surface of the tongue 250. The tongue engaging portion is desirably enlarged and can comprise one or more hemispherical tongue engaging bodies, such as of acrylic or other material that will not irritate the upper surface of the tongue. The tongue engager 302 is coupled to one or more elongated aims 304. More specifically, a distal end of the illustrated arm 304 can be downturned and embedded into the tongue engager 302. The main body 308 of arm 304 is elongated in a front to back direction and is slidably received within a channel 309 of an arm retention slide block 310 mounted to the upper surface of support 104. The channel 309 is sized to provide a friction fit with arm 308 to prevent sliding of the atm in a longitudinal (fore to rear) directions while resisting such sliding in the absence of force being applied to the arm, such as by grasping and pulling on the tongue engager 302 when the tongue retainer is removed from the user's mouth. The housing 310 can be of a suitable material, such as acrylic, with the channel 309 formed therein. The channel can be formed, for example, by placing a mold element, such as a strip of rubber band of rectangular cross-section against the surface 104, forming the housing 310 and then removing the rubber band. The channel can alternatively be machined or otherwise formed in the housing 310. In the case of a channel 309 of rectangular cross-section, the arm 304 can also be of a rectangular cross-section.

The front end 312 of arm 304 opposite to the distal end 306 can have an upturned stop portion 315 that prevents the arm from being totally removed from the tongue retainer after installation. That is, stop 315 engages housing 310 to retain the arm against removal of the arm from the tongue retainer. The housing 310 can be reinforced, such as with stainless steel mesh, during its manufacture. As can be seen in FIG. 2, the illustrated arm 304 can have an arcuate shape that generally follows the contour of the rear surface of palate plate 104. The space between the roof of the user's mouth and the palate plate accommodates the arm. Moving the arm in either of the front to back or back to front longitudinal directions of arrows 314 respectively moves the arm deeper in to the user's throat or further toward the user's mouth, thereby adjusting the position of tongue engager 302 rearwardly or forwardly. To the extent the tongue engager 302 is moved rearwardly, it provides additional assistance in holding the tongue away from the airway. In addition, the arm 304 can be made of or comprise a bendable material, such as of a corrosion resistant material, with stainless steel being a specific example. As a result, the arm can be bent in downward and upward directions indicated by arrows 316 to move the tongue engager downwardly or upwardly to respectively push the tongue further away from the airway (if the tongue engager is moved downwardly in FIG. 2), or allow the tongue to encroach further into the airway (if the arm is bent upwardly in FIG. 2). Friction between the arm and the channel can be provided by the discrepancy in the curve between the elongated arm and the channel. For example, the channel 309 can be straight (e.g., with a flat upper ceiling) and the elongated arm can be curved. Alternatively, the arm can be straight and the channel can be curved to provide a discrepancy between the contours of these elements to increase the friction between these elements. As another alternative, friction can be increased by providing a roughened surface on the arm and channel. Other suitable mechanisms for preventing spontaneous motion of the tongue engager within a user's mouth can be used.

Figure 4:
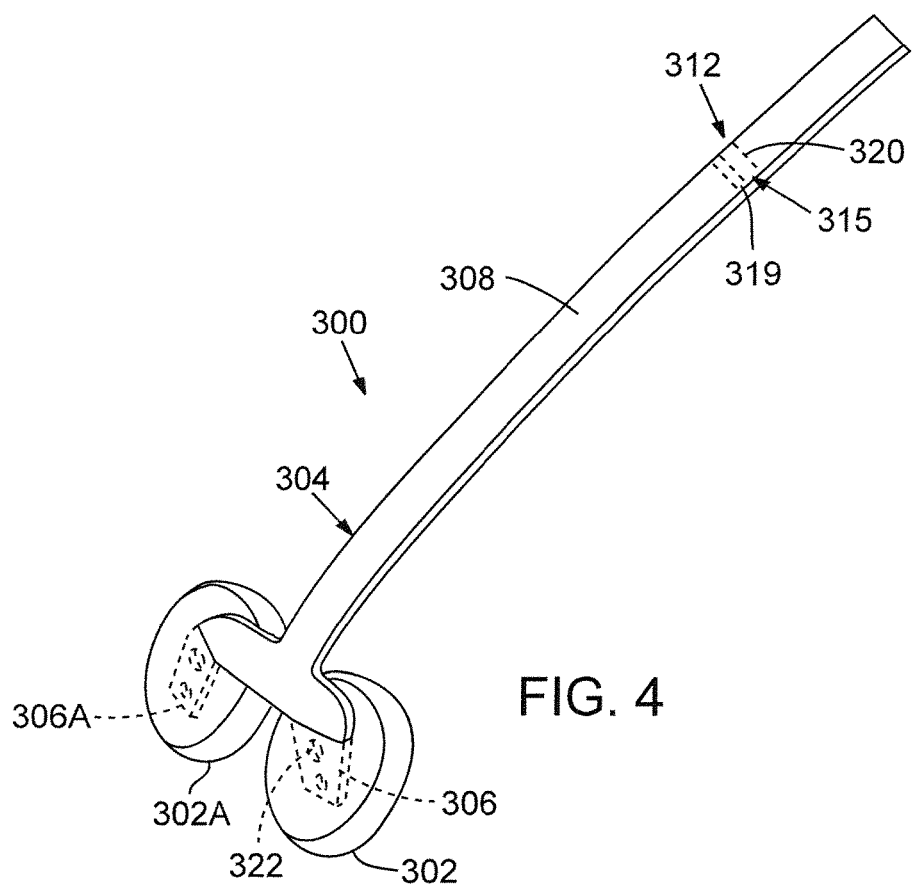
FIG. 4 illustrates one form of tongue depressor comprising an elongated arm with enlarged tongue engagers affixed to a distal end portion of the arm.

With reference to FIG. 4, an alternative embodiment of a tongue depressor 300 is shown. In FIG. 4, the same numbers have been used for like components discussed above in connection with FIG. 2 and hence will not be discussed further. In FIG. 4, the stop 315 can be formed by bending the arm 308 at location 319 to extend upwardly and then cutting the arm at location 320. The arm can be cut to a desired length for a particular individual user (e.g., a user with a large mouth can utilize a longer arm whereas a user with a smaller mouth can be fitted with a device having a shorter arm). In the embodiment of FIG. 4, the distal end portion of arm 308 is bifurcated and comprises first and second downwardly extending distal end portions 306, 306A having openings (one being indicated by the number 322) therein. These distal end portions 306, 306A can be inserted into the top of the tongue engagers 302, 302A and adhesively or otherwise secured in place. The openings 322 provide space for additional adhesive bonding connections. Alternatively, the tongue engagers 302, 302A can be molded around the distal end portions 306, 306A and cured.

In the illustrated embodiment, the arm 308 can be comprised of a unitary elongated panel of a durable corrosion resistant material, such as stainless steel shim stock, full hardness (stainless steel stock with a thickness of 0.02 inch being one specific example). The stop 315 can be produced with a bending tool after the arm 308 has been inserted through the channel 309 from the rear to the front of the channel. The stop prevents the arm from sliding completely through the channel so that detachment of the tongue arm and tongue engager from the tongue retainer is prevented.

In one specific foam, the tongue engagers 302, 302A can comprise two plastic hemispheres that can be spaced apart and positioned to contact the tongue on opposite sides of the mid-line of the tongue. This arrangement is advantageous because it is conducive to establishing an airway passage in the middle of the tongue where there is a natural groove between the muscle masses on both sides of the tongue. The positioning of a small space between the two hemispheres, (e.g., the tapered space between adjacent surfaces of the hemispheres that diverge from one another moving away from the tongue) is not easily occluded by soft tissue of the tongue. The hemispheres can be secured to the arm, such as using liquid acrylic (such as dental acrylic) with the openings 322 (desirably at least one per distal arm section 306, 306A) enhancing secure engagement when the acrylic cures.

Figure 5:
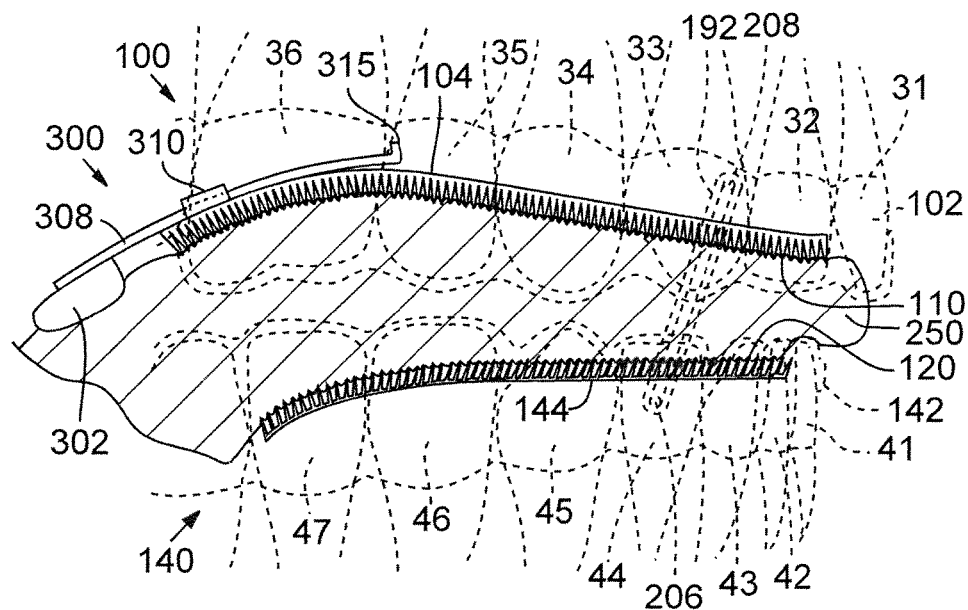
FIGS. 5 and 6 illustrate one form of tongue retainer with an exemplary tongue depressor shown in a first position in FIG. 5 and adjusted to a second position in FIG. 6.
Figure 6:
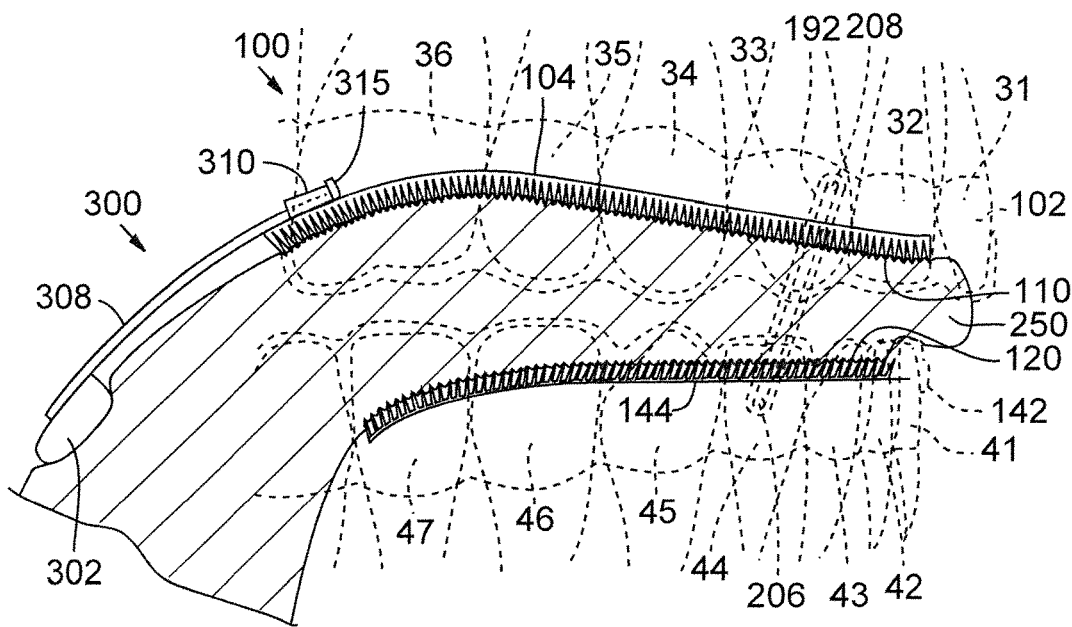

FIG. 5 illustrates the tongue depressor 302 in a first position similar to the position shown in FIG. 2 with the stop 315 moved somewhat closer to the user's mouth from its rearwardmost position. FIG. 6 illustrates the tongue depressor slid to its rearmost position with stop 315 engaging the housing 310. As one can see in FIG. 6, the tongue engager 302 is positioned deeper (rearwardly to a greater extent and downwardly to a greater extent) into the user's throat than when in the position shown in FIG. 5.

Figure 9:
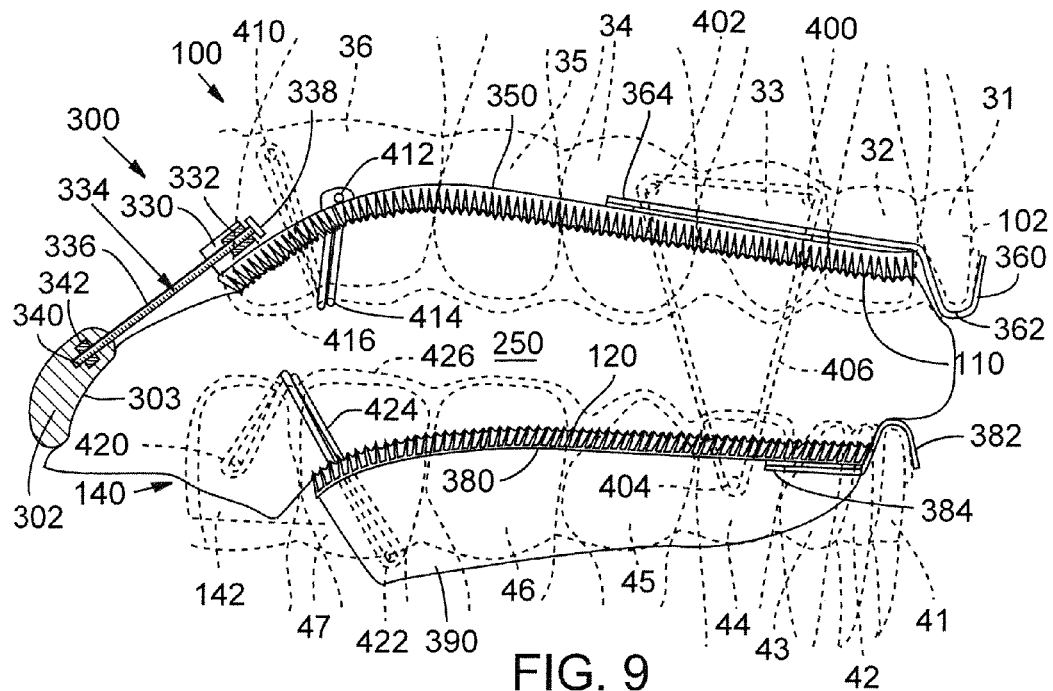
FIG. 9 illustrates the tongue depressor of FIG. 8 shown in a further downward and rearward position in engagement with a user's tongue.

FIGS. 7-9 illustrate an alternative form of tongue retainer and tongue depressor. Components in the FIGS. 7-9 examples that are like those in the FIGS. 1-6 examples have been given the same numbers and will not be discussed in detail. In the embodiment of FIGS. 7-9, a tube and rod mechanism has been eliminated for clarity and desirably would be included.

In the embodiment of FIGS. 7-9, the tongue depressor comprises a housing 330 having an internal cavity in which a nut or threaded sleeve 332 can be positioned in alignment with an axial opening extending through the threaded element 332 and housing 330. A tongue depressor support arm 332 comprising a threaded shank 336 is threaded through sleeve 332 and through the housing 330 to support the arm for axial movement generally in fore and aft directions relative to the user's mouth. As can be seen in FIG. 7, the opening through housing 330 is angled somewhat downwardly. An end 338 of arm 334 nearest the user's mouth is enlarged to form a stop and prevent the arm from being threaded entirely through the housing. That is, head 338 comprises a stop that limits the extent of downward and rearward axial motion of the arm 334. A tongue depressor 302 is secured to the distal end 340 of arm 334. The distal end can be inserted into an opening bored or otherwise provided in tongue depressor 302 and adhesively or otherwise secured in place. A nut or other enlargement 342 can be inserted onto the distal end 340 to resist separation of depressor 302 from the arm after these components are secured together, such as by acrylic.

With this construction, and with the tongue retainer removed from the user's mouth, rotation of the tongue depressor 302 in one direction rotates the atm 334 in the corresponding direction and shifts the shank axially to thereby move the tongue depressor portion 302 in a first direction, such as generally toward the user's mouth. Rotation of the tongue depressor portion 302 in the opposite direction shifts the shank and tongue depressor axially in the opposite direction (e.g., downwardly and rearwardly) to thereby adjust the position of the tongue depressor. The tongue depressor 302 is desirably of sufficient width (such as in the form shown in FIG. 4 with a pair of hemispheres or a paddle-like structure) so that the tongue depressor 302 will not rotate spontaneously in the user's mouth. FIG. 8 shows the tongue depressor rotated (again, this rotation would take place outside of the user's mouth) in one direction as indicated by the fact the tongue depressor 302 is inverted in FIG. 8 as compared to the position shown in FIG. 7. FIG. 9 illustrates the tongue depressor shifted axially to nearly its rearwardmost and downwardmost position.

As in the case of the embodiments of FIGS. 1-6, because the upper tongue gripping surface of the tongue retainer extends a substantial distance toward the rear of the tongue, significant additional structure is not needed to support a tongue rear depressor when a tongue rear depressor is mounted to the upper support for the tongue gripping elements. In addition, because the force pushing the upper tongue gripping surface into the tongue is resilient as a result of the biasing elements, the tongue rear depressor and upper tongue gripping surface can move with the tongue during swallowing when airway protection (to prevent blockage thereof) is not needed.

In the embodiment of FIG. 7, the upper support 350 for the tongue gripping surface 110 is coupled to the upper jaw coupler 102 so as to permit movement of the upper support 350 relative to the upper jaw coupler. More specifically, in this example, the support 350 can move upwardly and downwardly with the motion of the tongue to maintain contact with the tongue until such time as the mouth is opened wide enough to permit removal of the tongue retainer. More desirably, the upper support 350 is pivotally coupled to the upper jaw coupler, such as to a front portion of the upper jaw coupler. As one specific example of a pivotal connection, a tether 360 is shown extending from the front portion of the upper jaw coupler beneath the front tooth 31 and covering portion 362 of the upper jaw coupler and across the upper surface of the upper support 350 to a location 364 at which the tether is secured to the upper surface of upper support 350. The tether can comprise any suitable material, such as one or more strips of flexible mesh of a polymer material, such as described in greater detail below. Tether connection location 364 is desirably intermediate to or between the front and rear ends of the upper support 350 and is more desirably at a location that ranges from a central portion between the front and rear ends of the upper support 350 to a rear portion of the upper support. With this construction, if the lower jaw of the user drops, for example during sleep, both the front and rear portions of the upper support (as well as the central portion thereof) can also drop to maintain contact between the gripping elements of tongue gripping surface 110 and the upper surface of the tongue. In addition, if the mouth is opened widely, the tongue will be free of both the upper and lower tongue gripping elements 110, 120 to permit removal of the tongue retainer.

Figure 7A:
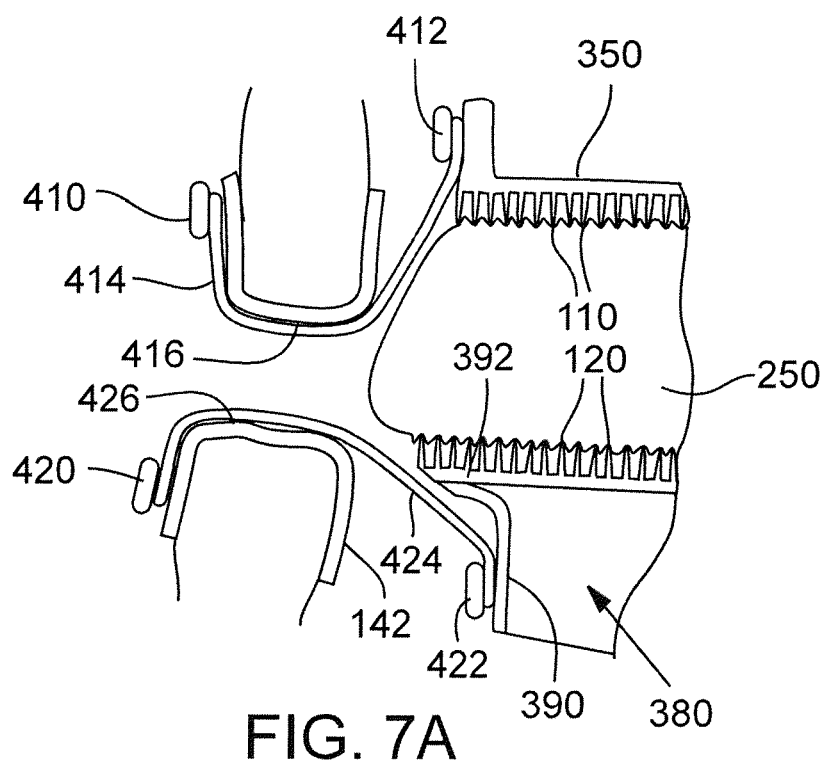
FIG. 7A is a vertical sectional view through a portion of the tongue retainer of FIG. 7 illustrating a biasing mechanism that can be used to couple rear portions of the respective upper and lower tongue gripping surface supports to their associated jaw couplers.
Figure 7B:
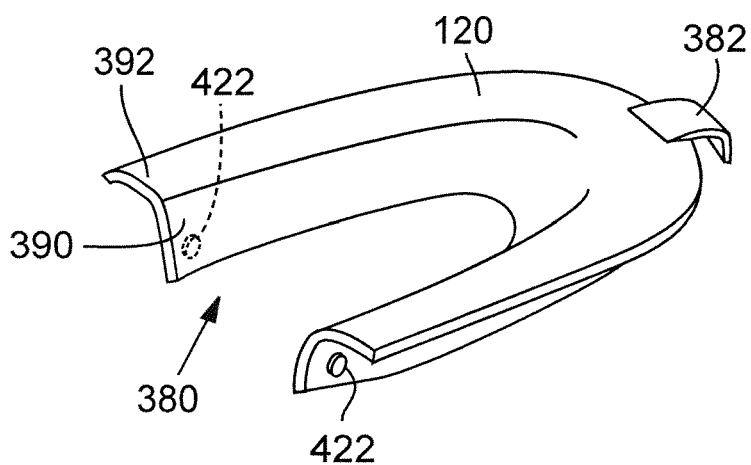
FIG. 7B is a perspective view of one form of a lower tongue gripping surface support.

Also, in the embodiment of FIG. 7, the lower gripping surface support 380 and the supported tongue gripping surface 120, can be fixed to the lower jaw coupler or alternatively, can be movably coupled to the lower jaw coupler. For example, the lower support 380 can be pivoted to the lower jaw coupler, such as by a tether 382 embedded or otherwise secured to the lower jaw coupler and to the lower support 380. For example, a tether can be secured to the lower jaw coupler at a location forwardly of the front of the lower jaw coupler, such as forwardly of the frontmost tooth 41 and can extend rearwardly across the biting surface of a lower tooth covering portion of the lower jaw coupler to a location 384 that can be at or spaced rearwardly of the front edge of the lower support 380. Since the tongue moves with the lower jaw, the lower support 380 naturally remains in contact with the tongue as a user opens his or her mouth slightly during sleep. For this reason, the tether 382 can be connected more forwardly to the undersurface of the lower support 380 than the location 364 of connection between tether 360 and the upper surface of upper support 350. As can be seen in FIG. 7B, the lower support 380 can be of a generally U shape construction with a downturned lingual flange portion 390 that is positioned along the sides and underneath the user's tongue and with an upper flange portion 392 which can support the tongue gripping elements of gripping surface 120.

Although different biasing elements can be used, in the illustrated embodiment of FIGS. 7-9, spaced apart projections, such as band coupling buttons 400, 402, extend outwardly from the buccal side of the upper jaw coupler 102 and a similar projection, such as a button 404, extends outwardly from the buccal side of the lower jaw coupler. An elastic band 406 engages each of the buttons 400, 402 and 404 to provide a biasing force for the front end of the jaw couplers. Like projections and biasing elements are also desirably provided at the opposite sides of the tongue retainer. Biasing elements interconnecting the two jaw couplers can be eliminated in embodiments such as described below.

In addition, projections such as a button 410 at the buccal side of a rear portion of the jaw coupler 102 and a button 412 at the outer side of upper support 350 are provided. An elastic band 414 extends from button 410 at the buccal side of the upper jaw coupler, across the biting surface 416 of the jaw coupler and to the button 412. This provides a downward biasing force to the upper jaw coupler upper support surface 350 at a rear portion thereof. In addition, a projection, such as a button 420, extends outwardly from the buccal side of a rear portion of the lower jaw coupler 142 and a projection, such as a button 422, extends outwardly from the outer surface of the flange 390 of lower support 380. An elastic band 424 extends from button 420, across the biting surface 426 of the lower jaw coupler and to the button 422 to provide an upward force to the lower support 380 to urge the rear end of the lower support against the user's tongue. Like projections and biasing elements are desirably provided at the opposite side of the tongue retainer for coupling the lower support 380 to the lower jaw coupler 140.

It should be noted that other biasing elements and biasing element positions can be used. Also, in the case of a lower support fixed to the lower jaw coupler, the lower biasing element at the rear of the coupler can be eliminated.

FIG. 7A illustrates a rear portion of the tongue retainer of FIG. 7 showing the connection of these exemplary biasing elements in greater detail. It should be noted that the opposite side of the tongue retainer can be the mirror image of the above described side.

In the embodiment of FIGS. 7-9, the upper tongue gripping surface 110 comprises gripping elements that are continually biased downwardly onto the top (dorsal) surface of the tongue by the biasing elements. The adjustable tongue rear depressor 300 in this embodiment is mounted, at least in part and desirably entirely, to the upper surface of the upper support 350. The tongue depressor 300 extends rearwardly and downwardly from the rearmost end of the upper support in a position to hold down the rear portion of a tongue to minimize the possibility of the rear of the tongue making contact with the soft palate and closing off the airway.

As best seen in FIG. 7, a form of tongue depressor 302 can comprise a concave tongue contacting surface 303 that is fixed to the rear or distal end of the externally threaded connecting arm 334. As mentioned above, connecting arm 334 can engage an internally threaded housing 330 (or threaded sleeve 332 positioned therein) positioned adjacent to the rear edge of the upper surface of the upper support 350. Desirably, in one form, the tongue contacting surface 303 has a curve that is similar to the curve of the rear of the tongue in a forward to backward direction. Because of such concavity in a forward to backward direction, the tongue contacting surface resists rotation of the tongue engager when the tongue engager is in the user's mouth and engaged by the rear of the tongue. When the tongue retainer is not in the user's mouth, the tongue engager 302 can be rotated by the user as previously described to adjust the effective length of the connecting arm 334 and thereby adjust the distance between the tongue contacting surface 303 and the upper tongue gripping surface 110 from which it extends rearwardly.

Figure 10:
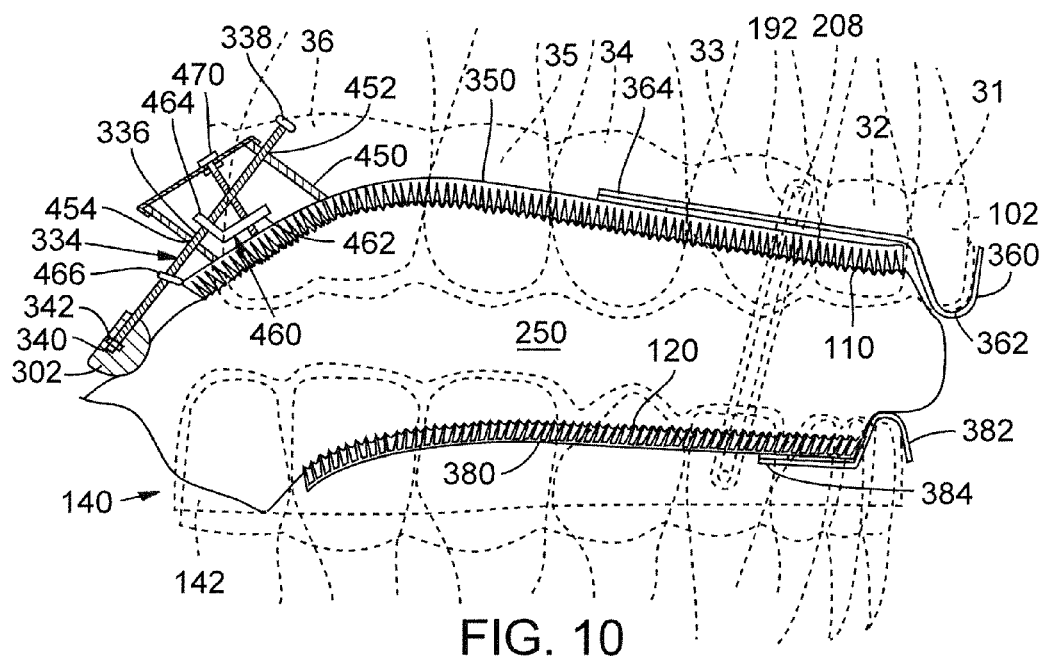
FIGS. 10 and 11 illustrate alternative forms of a tongue depressor shifted to respective different positions.
Figure 11:
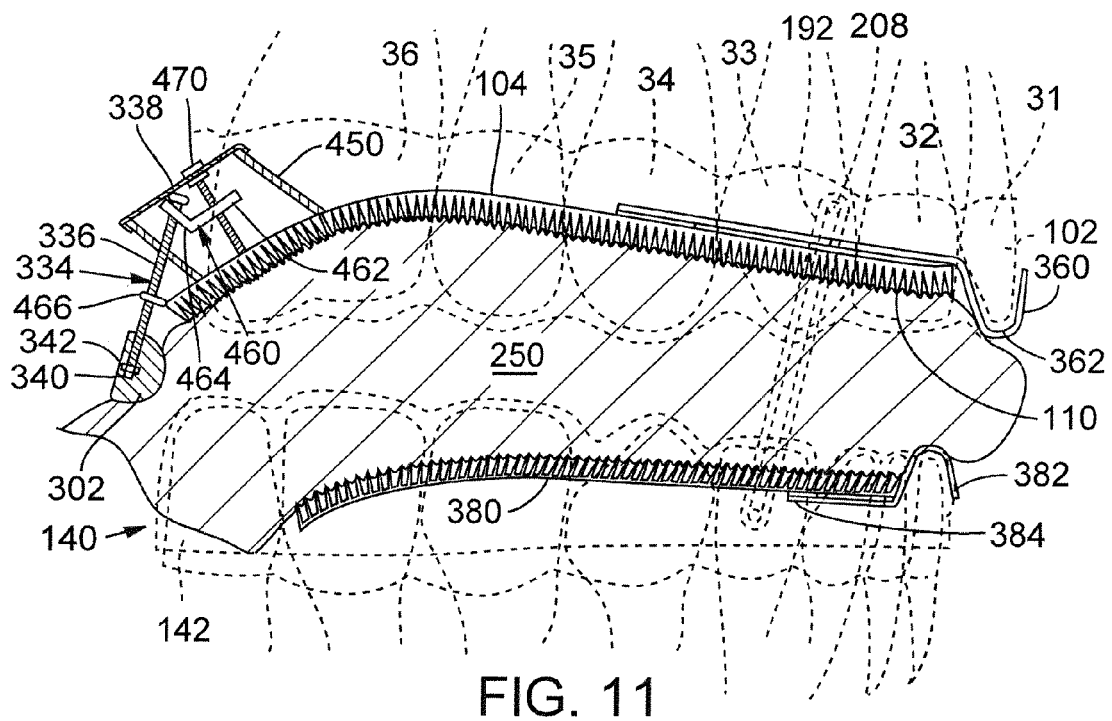
Figure 12:
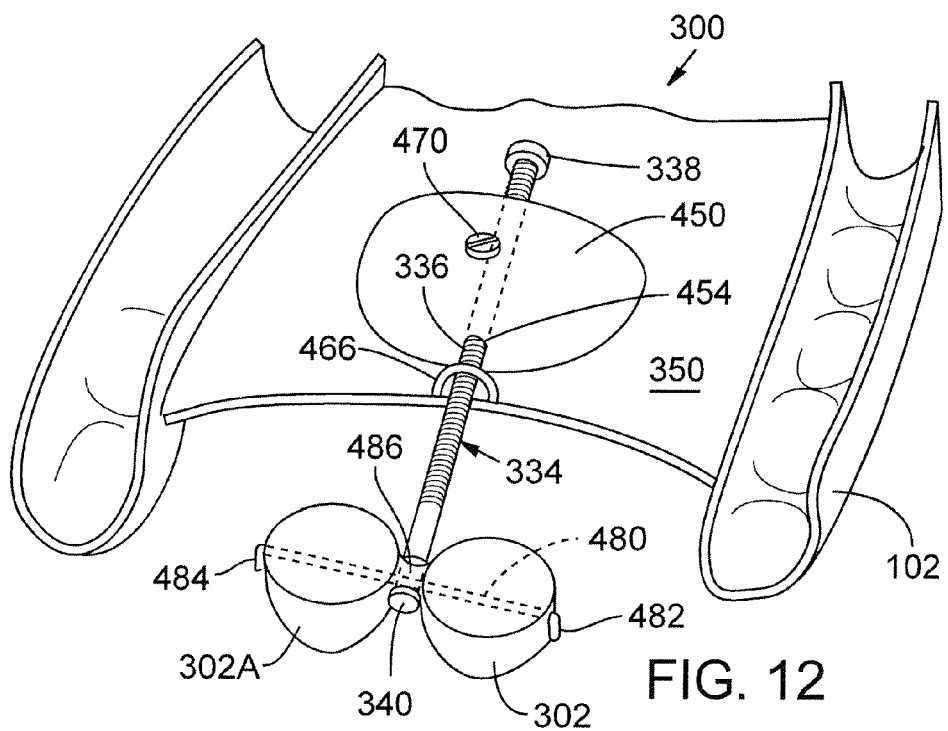
FIG. 12 illustrates yet another form of tongue depressor shown coupled to the upper surface of an upper tongue gripping surface support.

FIGS. 10-12 illustrate alternative embodiments of a tongue depressor. In the embodiment of FIG. 10, a housing 450 is shown mounted to the upper surface of the upper support 350. The arm 334 is shown extending through housing 450 and more specifically passing through openings or slots 452, 454 in front and rear walls of the housing. The slots 452, 454 desirably allow upward and downward movement of the arm 334 while preventing sideways or transverse movement of the arm. An arm support 460 is shown inside housing 450. In one form the support 460 is angular and comprises a first flange 462 and a second flange 464 angled relative to one another with the first flange being generally parallel to the upper surface of support 350 and the second flange 464 angling upwardly and rearwardly from the flange 462. The illustrated arm support 460 can take other configurations. The side edges of support 460 can engage the side walls of the housing so that the arm support is not rotatable within the housing. The arm 334 passes through a threaded opening in flange 464 and through a pivot 466 extending upwardly from a rear portion, such as the rear edge, of the support 350. Pivot 466 can comprise a ring or other structure that loosely receives a portion of the arm spaced from arm support 460. With this construction, rotation of arm 334 in one direction extends the tongue depressor 302 further into the user's mouth while rotation of the arm in the opposite direction shifts the tongue depressor further toward the front of the user's mouth. The support 460 also desirably carries atm 334 such that the arm is angled downwardly so that the upward and downward position of the tongue depressor is adjusted with the axial movement of the arm. Throughout this description, the terms "upwardly" and "downwardly" are determined with reference to the tongue retainer being in a user's mouth with the mouth being oriented substantially horizontally. Thus, these upward and downward directions will change if the orientation of the user's head changes, but still apply when evaluated with the tongue retainer in the referenced orientation. The structure of FIG. 10 comprises one mechanism that allows the adjustability of the angle of the arm and thereby the upward and downward position of tongue depressor 302. More specifically, a threaded element, such as a machine screw 470 is threadedly coupled to the top of housing 450 and to the flange 462 and into coupled engagement with the upper surface of upper support 350. The screw 470 can rotate relative to housing 450 but is retained by a stop from removal from the housing. As screw 470 rotates in one direction, the support 460 shifts axially in a first upward direction along the screw, thereby increasing the angle of the arm 334 relative to support 350 (e.g., raising the arm and lowering tongue engaging portion 302) whereas rotation of screw 470 in the opposite direction shifts support 460 axially in a second forward direction along the screw, thereby decreasing the angle of arm 334 relative to support 350 (e.g., lowering the arm to thereby raise the tongue engager 302). The adjusting screw 470 can be smaller in diameter than the diameter of connecting arm 334. To stabilize the position of the lower end of the screw 470, the screw can be rotatably attached at its lower end to the upper surface of the upper support 350 by, for example, a metal plate that engages an annular groove near the bottom end of the machine screw to rotatably support the machine screw and prevent its removal from the housing. The machine screw can exit through the top or cap of the housing with a seal provided at that location, such as using tubing, with acrylic tubing being one specific example that surrounds the machine screw and bracket 460 to protect them. The head of the machine screw 470 can have a tool receiving recess, such as a screwdriver receiving slot, so that it can readily be turned in the desired direction. Other mechanisms can be used to raise or lower the arm 334 to adjust the upward or downward position of the tongue engager 302. For example, a wedge that can be drawn progressively inwardly or outwardly underneath the bracket 460 can be used. Alternatively, the top of the housing can be removed and wedges or spacers placed underneath the bracket to adjust the angle with the top thereafter being replaced.

The pivot 466 can comprise a ring that is slightly larger than the diameter of the connecting arm 334 so that the connecting arm can rotate within the ring as well as pivot upwardly and downwardly relative to the ring. The ring can comprise a loop of wire, the ends of which are connected to the upper support, such as embedded in acrylic on the upper support 350. The pivot can be formed by other devices that define an opening that desirably has reinforced upper and lower edges that can be attached to the upper support 350. When the rear of the user's tongue pushes upwardly on the tongue engaging elements 302, the tongue pushes up on the connecting arm 334.

In the embodiment of FIG. 11, the head end 338 of arm 334 is shown positioned entirely within the housing 450. In this case, adjustment of the front to rear position of the tongue depressor 302 is accomplished by rotation of the tongue depressor to axially shift the arm 334 relative to bracket 460 in front or rear directions. In FIG. 11, a support bracket 460 has been raised to its fullest extent to provide the steepest angle of the arm 334 in the downward direction.

In the embodiment of FIG. 12, the housing 450 is of a generally rounded construction. In addition, first and second tongue engaging hemispheres 302, 302A are shown mounted to the distal end 340 of the arm 334. To securely attach the hemispheres 302, 302A, in place, a pin 480 can pass through each of the hemispheres and through an opening in the distal end 340 of arm 334 with the ends 482, 484 of the pin 480 being bent downwardly to secure the hemispheres in place. Acrylic is shown bonding the hemispheres together as indicated at 486. The pin ends 482, 484 can also be bonded to the hemispheres, such as using acrylic.

Figure 12A:
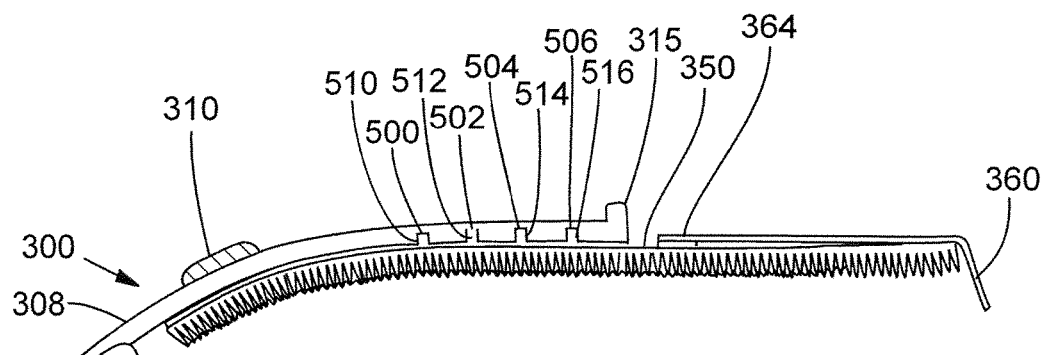
FIGS. 12A and 12B illustrate a still further form of tongue depressor with FIG. 12A showing the tongue depressor in a latched position and FIG. 12B showing the tongue depressor in an unlatched position allowing the tongue depressor to be shifted forwardly or rearwardly, as well as upwardly and downwardly, relative to the rear of the upper tongue gripping surface support.
Figure 12B:
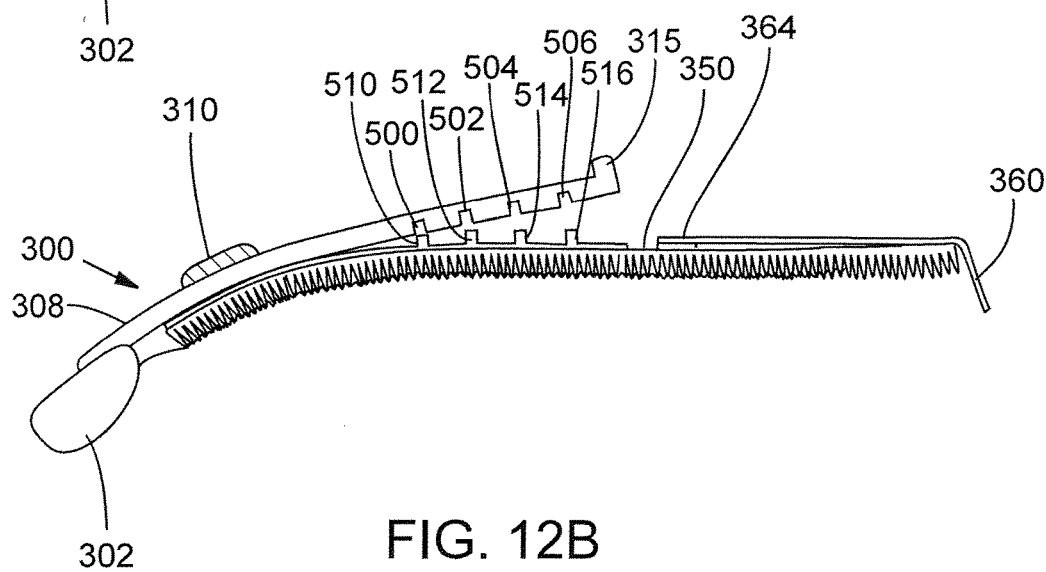

Yet another embodiment of a rear tongue depressor is shown in FIGS. 12A and 12B. Components in common with the embodiments of FIGS. 2 and 7 have been assigned the same numbers. In the embodiment of FIGS. 12A and 12B, the arm 308 passes through a channel in housing 310 and is slidable in opposed front to rear directions through the housing. A stop 315 of greater cross-sectional dimension than the channel prevents the tongue depressor from being detached from the tongue retainer. The arm 308 in this example comprises a curved bar slidably mounted to the rear of the upper support 350 by passing through the housing 310 that is mounted to the upper surface of the upper support. The arm 308 comprises a number of intermeshing elements, such as notches 500, 502, 504 and 506, spaced along the length of the arm 308 and facing the upper surface of upper support 350. The intermeshing elements selectively interface with corresponding intermeshing elements provided on the upper surface of support 350, such as projections 510, 512, 514 and 516. In the form shown in FIGS. 12A and 12B, the notches 500-506 are rectangular box-like in shape and the projections 510-516 are of a corresponding rectangular box-like shape. The projections 510-516 engage the notches 500-506 when the tongue retainer is in place as upward pressure by the tongue on the tongue engager 302 tends to pivot the arm 308 upwardly to hold the notches and projections together. A biasing element, such as a rubber band can be used to urge the notches and projections together. To adjust the position of the tongue engager 302, with the tongue retainer removed from the user's mouth, the notches and projections can be disengaged, as shown in FIG. 12B. When disengaged, the arm 308 can be slid in a front to rear direction, or rear to front direction, to adjust the position of the enlarged tongue engager 302. Following this adjustment, the then-aligned notches and projections can reengage one another in the new position of the arm to thereby position the tongue engager 302 as desired.

The various tongue depressors as described above, as well as alternative embodiments thereof, desirably comprise devices that can be mounted to the upper support of a tongue retaining apparatus, with the tongue depressor positioned to urge the rear of the tongue away from the airway of the user. Desirably the tongue engager is adjustable in front to rear and rear to front directions as well as upwardly and downwardly relative to a tongue gripping support of a tongue retainer.

An alternative form of tongue retainer is shown in FIGS. 13A-13E. This embodiment has some elements in common with the embodiment of FIG. 7. These common elements have been given the same numbers in FIGS. 13A-13E as assigned to them in FIG. 7 and will not be discussed in detail. The embodiment of FIGS. 13A-13E is desirably provided with an adjustable tongue depressor as previously described. However, for purposes of convenience a tongue depressor is not shown in FIGS. 13A-13E and this embodiment, as well as other tongue retainer embodiments disclosed herein, will function, albeit not as well, without a tongue depressor. In the embodiment of FIGS. 13A-13E, the upper support 350 for the tongue gripping surface 110 is shown pivoted to the upper jaw coupler 102, such as by a tether 360 so as to permit the upper support to move upwardly or downwardly with the movement of the tongue and more desirably to permit both the front and rear portions of the upper support to move with the upward and downward movement of the tongue until such time as a user's mouth is opened wide enough to permit removal of the tongue retainer. Similarly, the lower support 380 can be pivoted, such as by a tether 382, to the lower jaw coupler 142. As previously explained, the tether 382 can extend from a front portion of the lower jaw coupler to a front portion of the lower support 380. In addition, the tether 360 desirably extends from the front of upper jaw coupler 102 to a location 364 spaced inwardly from the front edge of the upper support 350. In an alternative construction, the lower support 380 can be fixed to the lower jaw coupler.

In the embodiment of these figures, a biasing projection extends upwardly from the upper surface of upper support 350 with one such biasing projection being indicated at 520 in these figures. The biasing projection comprises a bias engager, such as a band engaging button 522 projecting upwardly therefrom. A bias member engaging projection, such as a band engaging button 524, projects outwardly from the buccal surface of the upper jaw coupler at the side 523 of the upper jaw coupler near the rear end of the upper jaw coupler. A similar bias member engager, such as a button

Figure 13A:
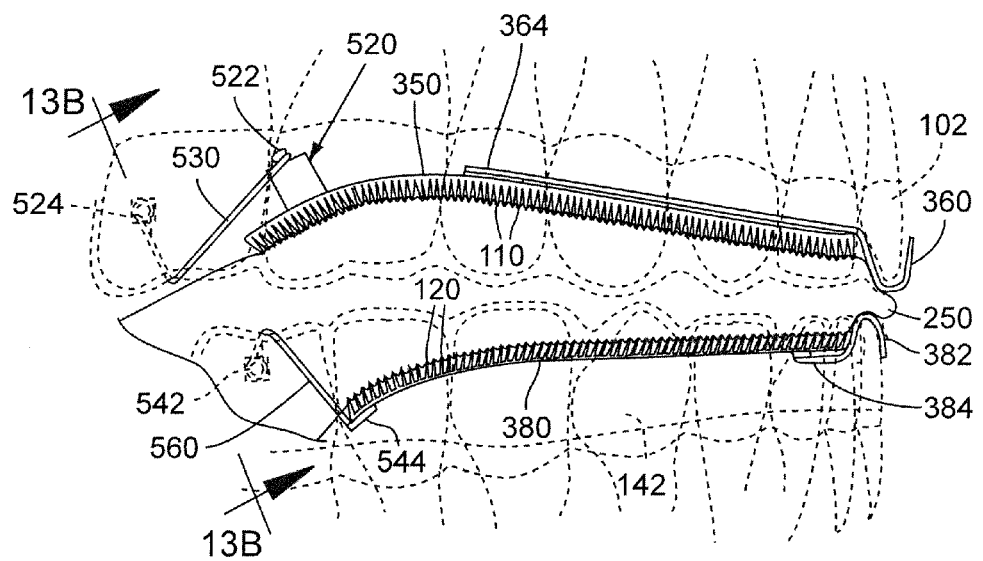
FIG. 13A illustrates an alternative form of tongue retainer in which a biasing member urges a pivotal upper tongue gripping surface support downwardly and another biasing member urges a lower tongue gripping surface support upwardly, the lower support being pivotally coupled to the lower jaw coupler, it being understood that a tongue depressor can be included in the embodiment of FIG. 13A and that tube and rod mechanisms, such as shown in FIG. 1, can also be included in the embodiment of FIG. 13A.
Figure 13B:
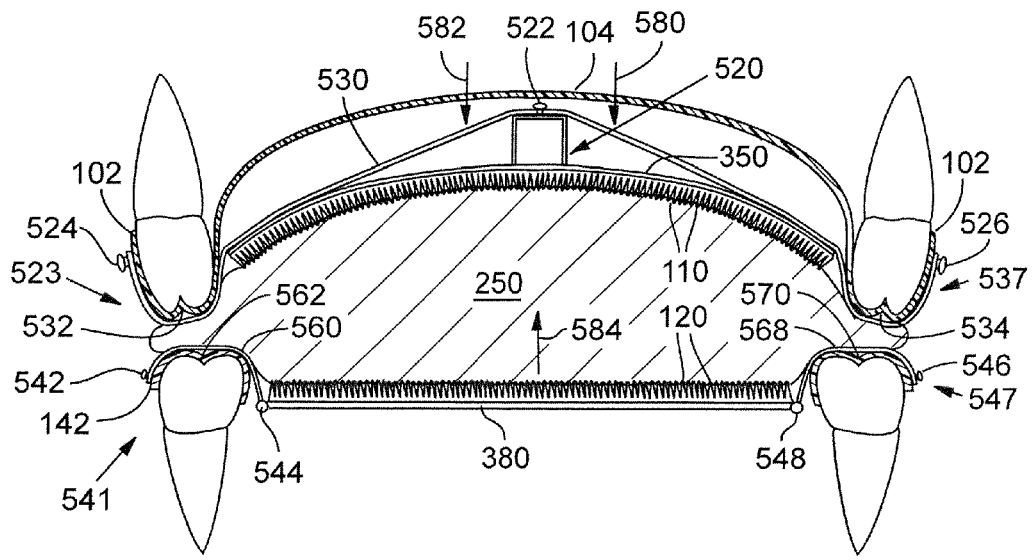
FIG. 13B illustrates a transverse cross-sectional frontal view of the embodiment of FIG. 13A.

526, projects outwardly from the buccal surface of the upper jaw coupler at the side 537 of the upper jaw coupler adjacent to the rear of the lower jaw coupler. One or more biasing members, such as an elastic band 530 interconnects these bias member engagers 524, 522 and 526 (see FIG. 13B). As can be seen in FIG. 13B, the band 530 extends from button 524 at the buccal side 523 of the upper jaw coupler 102, across the biting surface 532 of the upper jaw coupler, across the upper surface of upper support 350 and into engagement with the button 522. From button 522, the band 530 extends across the upper surface of upper support 350 and across the biting surface 534 of the jaw coupler 102 at the side 537 of the jaw coupler 102 opposite to the side 523.

In addition, a projection, such as a button 542, extends outwardly from the buccal side of a first side 541 of the lower jaw coupler 142 and a biasing member connector, such as a button 544, is coupled to the lower support 380. A similar biasing projection 546 projects outwardly from the buccal surface of lower jaw coupler 142 at the second side 547 of the lower jaw coupler opposite to side 541. Also, a biasing member connector 548 is provided at the side of the lower support 380 opposite to the side containing biasing member connector 544. A first biasing member, such as an elastic band 560, extends from button 542, across the biting surface 562 of lower jaw coupler 142 at side 541 thereof to the connector 544. In addition, a biasing member 568, such as an elastic band, extends from button 546, across the biting surface 570 of the lower jaw coupler at side 547 thereof to the biasing member connector 548.

For purposes of convenience in illustration, the lower support 380 in FIG. 13B is shown straight although it would typically be curved to fit the contours of the user's mouth beneath the tongue 250. With this construction, when the user's mouth is closed, such as shown in FIGS. 13A and 13B, a downwardly directed biasing force, as indicated by arrows 580, 582, is applied to the upper surface of the upper support 350 to urge the gripping elements of the tongue gripping surface 110 against the upper surface of tongue 250. In the same manner, the biasing members 560, 568 apply an upward biasing force, as indicated by arrow 584, against the lower surface of the tongue. As a result, the user's tongue is gripped between the tongue gripping surfaces 110, 120. If the lower support 380 is fixed to the lower jaw coupler 142, the biasing members 560, 568 are eliminated and the biasing force is applied from above. The projection 520 desirably elevates the biasing member such that it is stretched to a greater extent and applies a greater downward biasing force when the user's mouth is closed.

Figure 13C:
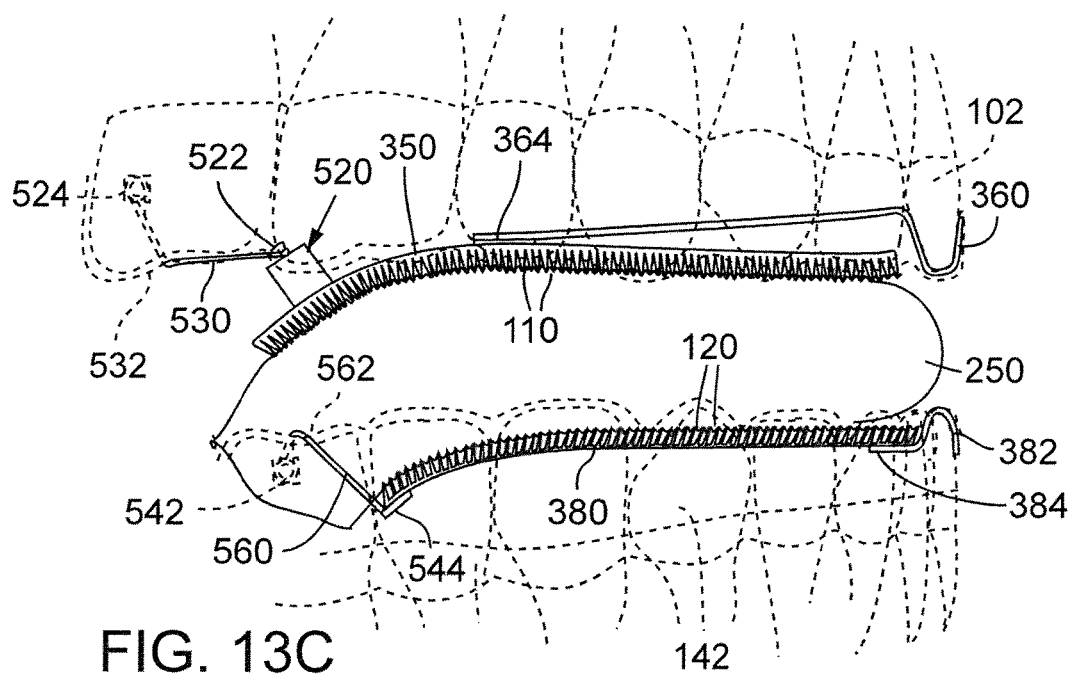
FIG. 13C illustrates the embodiment of FIG. 13A with a user's mouth opened slightly, thereby illustrating the tongue retainer's continued gripping of the tongue.

FIG. 13C illustrates the user's mouth in a partially open state, such as when the user swallows or the user's mouth shifts slightly during sleep. In this case, the biasing member 530 is almost level within the user's mouth indicating the reduction of force on the user's tongue. However, the pivot, in this case the tether 360, has allowed the upper support 350 to move downwardly, and more desirably both the front and rear portions of the upper support have been allowed to move downwardly, so as to maintain contact with the tongue and retain the tongue in its forward position despite the partial opening of the mouth.

Figure 13D:
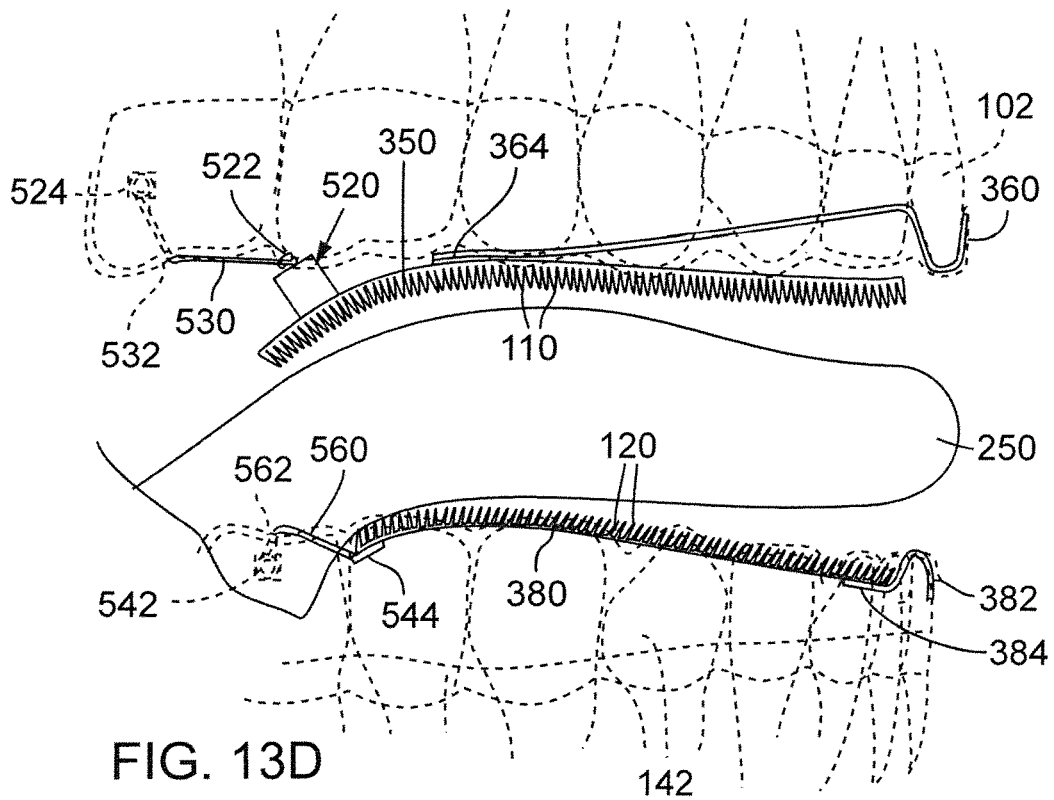
FIG. 13D illustrates the embodiment of FIG. 13A with the user's mouth more fully opened to release the tongue to permit removal of the tongue retainer from the user's mouth.
Figure 13E:
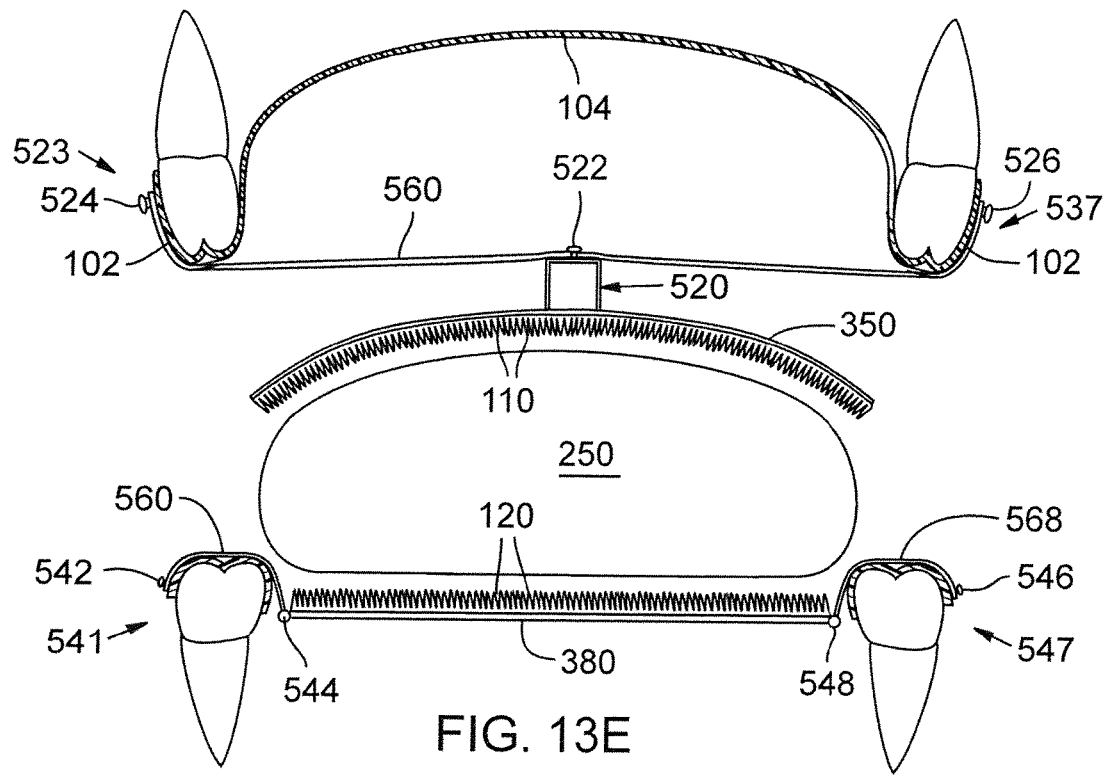
FIG. 13E shows a transverse cross-sectional frontal view of the embodiment of FIG. 13D with the user's mouth more fully opened.

FIGS. 13D and 13E illustrate the mouth in a more fully open position. In this case (as can be seen in FIG. 13E), the elastic band 530 extends directly across the user's mouth without applying a downward biasing force, which facilitates the removal of the tongue retainer from the user's mouth.

In the embodiment of FIGS. 13A-13E, desirably there are no biasing members, such as rubber bands connecting upper and lower components of the tongue retainer. Consequently, wide mouth opening is not restricted by rubber bands or other biasing elements. In the illustrated construction, the tongue retainer employs intra-arch biasing members, such as one or more rubber bands connecting the upper dental appliance or jaw coupler with the upper tongue gripping surface for support. In addition, intra-arch rubber bands connect the lower dental appliance or lower jaw coupler with the lower tongue gripping surface or lower support in the case of a pivotal lower support. Because the intra-arch rubber bands have a first end located near or passing across the bite surface of the associated jaw coupler and a second end attached to the tongue gripping surface or to an extension of the tongue gripping surface at a location removed from the plane of the bite table, moderate to wide mouth opening brings the second end close to the first end (close in elevation of the first end) and thereby eliminates or substantially eliminates the bias of the biasing member or rubber band pushing the tongue gripping surface against the tongue to thereby facilitate the release of the tongue retainer by the user.

To bias the upper tongue gripping surface or upper support away from an arch plate of the upper jaw coupler, the biasing member, such as rubber bands connecting the upper jaw coupler to the upper support desirably have one end portion attached so as to cross the bite surface of the upper jaw coupler and another portion attached to a palatal flange, bracket or other extension structure that projects upwardly from the upper support and away from the tongue gripping surface toward the hard palate. In addition, by using a pivot, such as a tether with the upper tongue gripping surface support attached to the tether at a location in a mid or rear portion of the upper support and with the opposite end of the tether coupled to a front portion of the upper jaw coupler, significant mouth opening can occur without pulling the upper tongue gripping surface 110 away from the upper surface of the tongue as the tongue descends with the lower jaw bone during jaw opening.

To bias the lower tongue gripping surface upward against the underside of the tongue (if the lower tongue gripping surface is not fixed to the lower jaw coupler), and away from the lower jaw coupler, biasing members, such as rubber bands can be used. These bands can have one end attached to a lower portion of a lingual flange portion of the lower tongue gripping surface (such as located deep in the floor of the mouth, see flange portion 390 in FIG. 7B) and the other end connected to the lower jaw coupler at a location near or across the bite surface of the lower jaw coupler. In the case of a movable lower support surface, a short tether can be used because the tongue moves with the lower jaw bone on opening of the mouth. The above construction provides a mechanism for biasing the upper and lower tongue gripping surfaces against the surface of the tongue in a manner that allows easy disengagement from the tongue by the user upon wide opening of the user's mouth while still minimizing the possibility of inadvertent tongue release during the small mouth opening movements that often occur during sleep.

The pushing of either or both tongue gripping surfaces away from the associated jaw couplers and into the adjacent surfaces of the tongue is accomplished in some desirable embodiments by having biasing members, such as rubber bands, stretched between or across the bite surface of the associated jaw coupler to a portion of the associated tongue gripping surface support that is located relatively far from the elevation of the bite surface of the jaw coupler. Thus, in the case of the upper support, an upwardly extending projection (e.g., projections 520) is provided for coupling to a biasing member, the upper projection being at an elevation above the elevation of the plane containing the bite surfaces 532, 534 (FIG. 13B) at opposite sides of the upper jaw coupler when the user's mouth is closed. The elevation is determined with reference to the tongue retainer in a horizontal orientation and the mouth of the user being closed. In addition, the lower support for the lower tongue gripping surface can have a downwardly extending structure, such as lingual flanges (e.g., 390 FIG. 7B) at the sides of the lower support that extend downwardly toward the base of the mouth to an elevation below that of the plane containing the lower biting surfaces (562, 570 FIG. 13B) of the two sides of the lower jaw coupler. Coupling biasing members to the downwardly extending lingual flange increases the upward biasing force against the lower surface of the user's tongue when the mouth is closed, yet permits relaxation of the biasing force when the mouth is open. Desirably, a tether from the front of the upper jaw coupler is attached to a mid portion or rear portion of the upper tongue gripping surface support so that the upper tongue gripping surface support can lower with the tongue a significant distance before pulling the tongue gripping surface away from the tongue.

The various components, such as the upper and lower supports can be made of a material such as dental acrylic to facilitate attachment to devices such as lingual buttons and mesh by embedding these components into the acrylic.

The illustrated tethers can be of any suitable material, such as one or more rectangular pieces of polymer meshes with polyester mesh being a specific example. Stainless steel mesh is also suitable, as would be other types of mesh, wire, loops or other flexible durable tethers, such as of materials used in orthodontics.

In one specific approach, the upper tether 360 (FIG. 13C) can be embedded into acrylic on the front facing surface of a respective upper jaw coupler 102 and the lower tether 382 can be embedded in the front facing surface of the lower jaw coupler 142. In connection with the upper tether, between the attachment of the tether to the front of the upper jaw coupler and its attachment to the upper surface of the upper support at a position (e.g., position 364) rearwardly of the front edge of the upper support, is an area of tether that remains free to move. The tether is desirably of a material that can flex or move to accommodate different tongue sizes or shapes and to move slightly with the tongue during swallowing. Desirably the tether is not of a significantly stretchable material.

In one desirable embodiment, the unembedded (free) length of tether between the lower tongue gripping surface and the front of the lower dental appliance is relatively short (for example, ¼ to ½ inch). The rear portion of the tether can be attached to the underside of the front portion of the lower tongue gripping surface support. In comparison, the unembedded (free) length of mesh between the attachment of a first end of the upper tether to a front portion of the upper jaw coupler and a second end of the upper tether to the upper support is desirably longer (e.g., ¾ to 1½ inch) than the free portion of the lower tether. This is because the second end of the upper tether is desirably attached to a middle or rear portion of the upper tongue gripping surface support. The relatively longer length of the free portion of the upper tether allows the entire upper tongue gripping surface to lower with the tongue and lower jaw bone during partial opening of the mouth. During such partial opening, the tether is in effect a pivot and rotates the upper tongue gripping surface around its attachment to the front of the upper jaw coupler. Desirably when the mouth is open so wide that the tether is nearly vertically oriented, the pull on the tether on the underside of the upper tongue gripping surface is sufficient to separate the descending tongue from the upper tongue gripping surface. At this same wide opening of the user's mouth, the bias of rubber bands (in an embodiment with such bands) that otherwise would push the upper tongue gripping surface down and away from the upper dental appliance against the tongue ceases because the two ends of the bands have become as close as possible [the band (or bands) has relaxed].

In one specific example, the bias of the respective tongue gripping surfaces against the associated surfaces of the tongue is provided by rubber bands, such as of the type typically used in orthodontics and called orthodontic elastics. The use of orthodontic elastic bands to provide the bias allows the user to adjust the bias by using shorter or longer elastic bands, since orthodontic elastic bands are available in a wide variety of lengths and thicknesses. Also, orthodontic elastic bands have historically been proven to be very safe since they have been used for many decades with few negative consequences.

Figure 14:
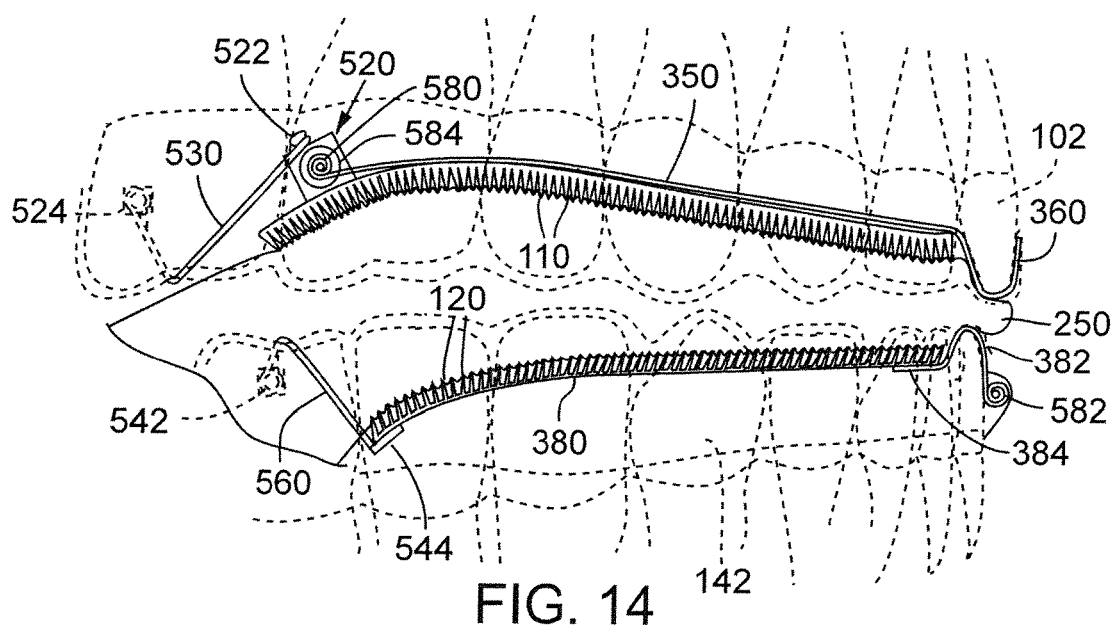
FIG. 14 illustrates an embodiment similar to FIG. 13 with variable length upper and lower tethers.

FIG. 14 illustrates an embodiment of a tongue retainer like the embodiment of FIGS. 13A-13E with several modifications. In the embodiment of FIG. 14, the upper tether 360 is adjustable in length. That is, the upper tether 360 can have additional tether material, such as a coil of tether material 580 positioned within structure 520. Similarly, the tether 382 can have additional tether material, such as a coil of such material 582 positioned in a small tether mesh receiving housing at the front of the lower jaw coupler. Thus, the tethers can be of variable length. In addition, a mechanism can be provided for adjusting the length of one or both tethers while retaining the tethers in a position to which they have been adjusted. For example, a small motor, such as a remotely controlled stepper motor 584, can be coupled to coil 580 for operation in response to control signals, such as wireless signals, to rotate the coil to either retract or extend the tether. This can be done, for example, during a sleep study to evaluate the impact of moving the position of the tongue. By shortening the upper tether with the tongue gripped by the upper and lower tongue gripping surfaces, the tongue will be moved forwardly relative to the jaw couplers to permit evaluation of the impact of this repositioning of the tongue on sleep apnea. The lower jaw tether can also be controlled by a motor or simply be placed under tension so that it lengthens or shortens with the movement of the tongue due to the change in the length of the upper tether since the lower tongue gripping surface is in engagement with the tongue. Other mechanisms can be used for rotating a spool of tether material, such as using a ratchet or string wound around the spool that can be pulled to rotate the spool.

As another embodiment, the biasing can be provided by a compression spring positioned to urge the upper tongue gripping surface away from a palate plate of an upper jaw coupler and against the surface of the tongue. For example, one end portion of a spring can be embedded in or otherwise secured to the underside (palate facing side) of the upper support at a location opposed to the upper tongue gripping surface with the opposite end of the spring secured to a palate or arch plate. An exemplary spring can be of a relatively large diameter ½ to ¾ inch) and ⅛ to ¼ inch long. Such a spring can be made of small diameter (e.g., 0.012-0.018 inch) thick stainless steel wire or other suitable material. A single large diameter spring provides flexibility as well as positional stability for the upper tongue grasping surface. But it is to be understood that multiple smaller diameter springs, such as three ¼ inch diameter springs can be used. In connection with the lower tether, desirably the length of the free portion of the mesh is at least ⅛ inch between the portion of the mesh that is embedded in the lower support and the lower support and the portion of the mesh that is embedded in the lower jaw coupler. In addition, desirably there is a gap of at least ½ inch of free mesh or tether between the end of the mesh that is embedded in the front of the upper jaw coupler and the rearmost end of the mesh that is embedded in a portion of the upper tongue gripping surface support.

Figure 15:
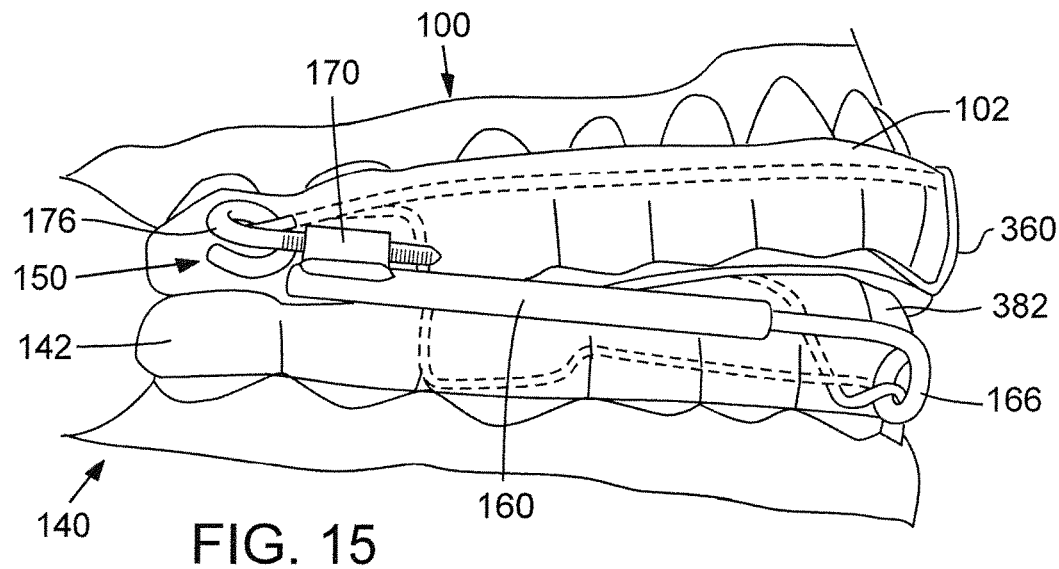
FIG. 15 illustrates yet another form of tongue retainer having an upper tongue gripping surface support pivoted to an upper jaw coupler and a lower tongue gripping surface support fixed to a lower jaw coupler.
Figure 16:
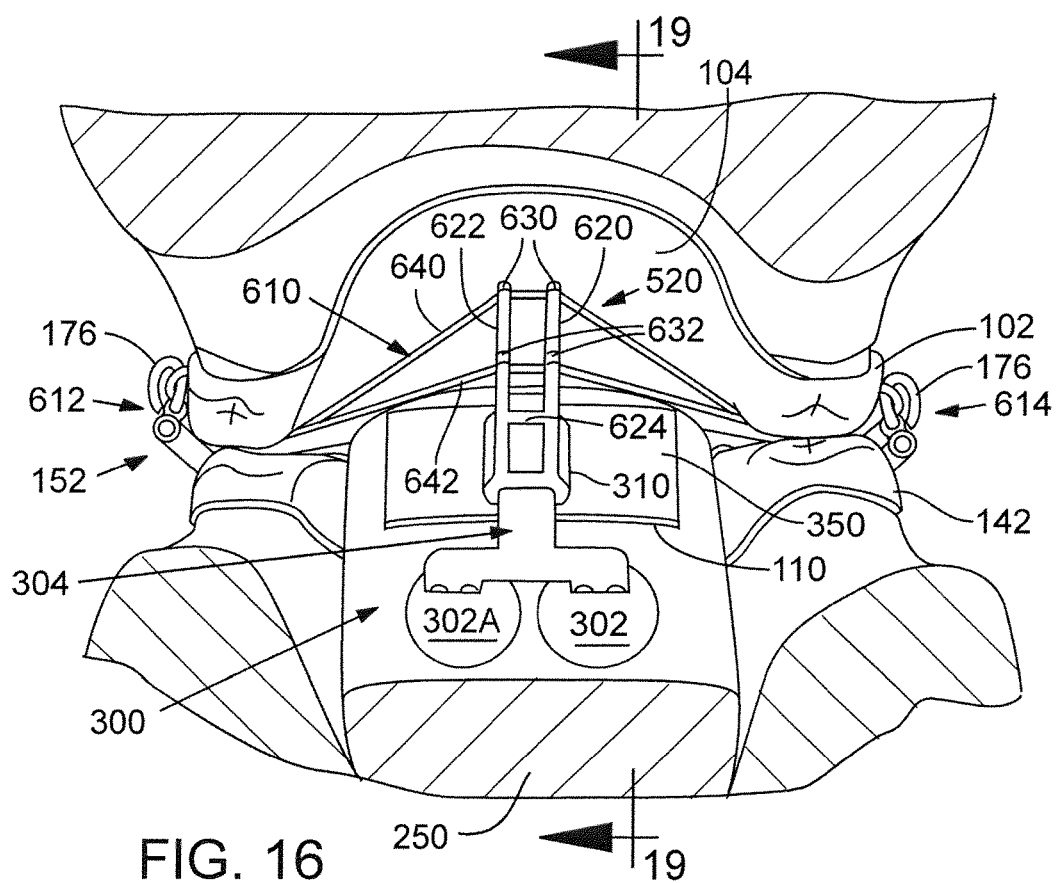
FIG. 16 is a view of the tongue retainer of FIG. 15 looking from the rear of a user's mouth.
Figure 17:
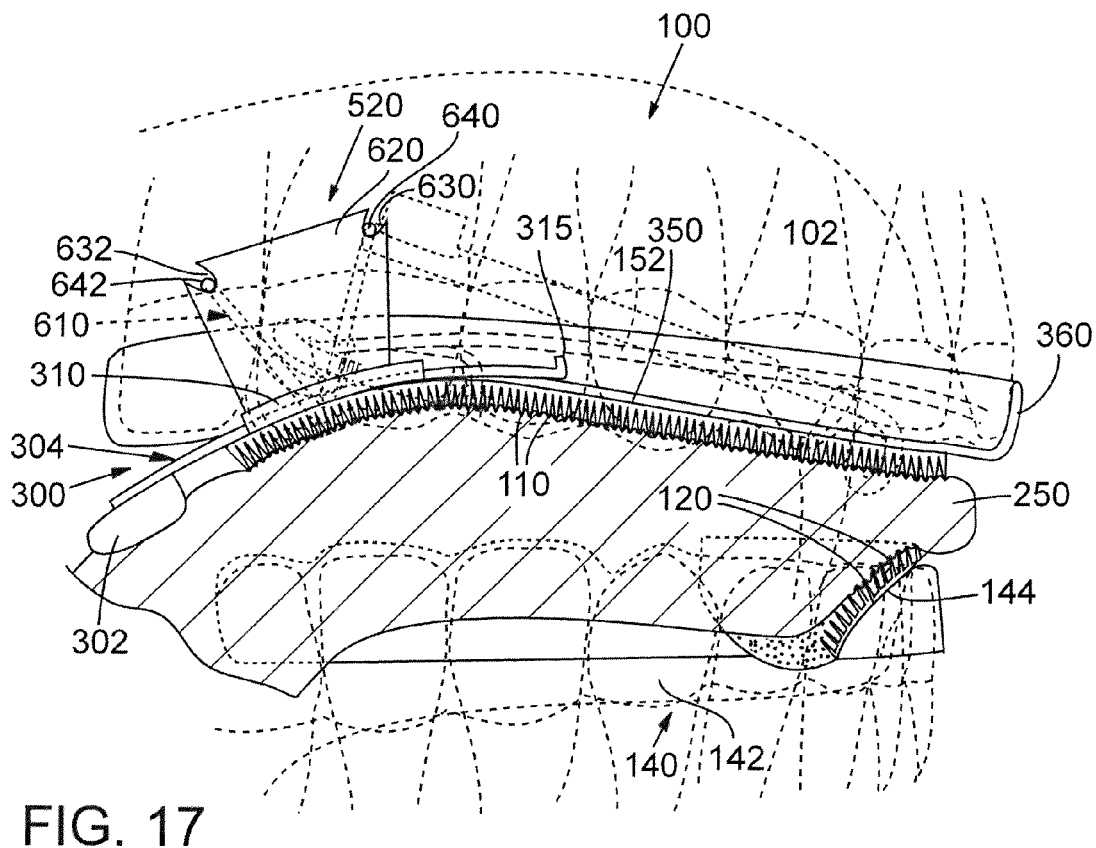
FIG. 17 is a vertical sectional side elevational view through a portion of the embodiment of FIG. 15 shown positioned in a user's mouth.
Figure 18:
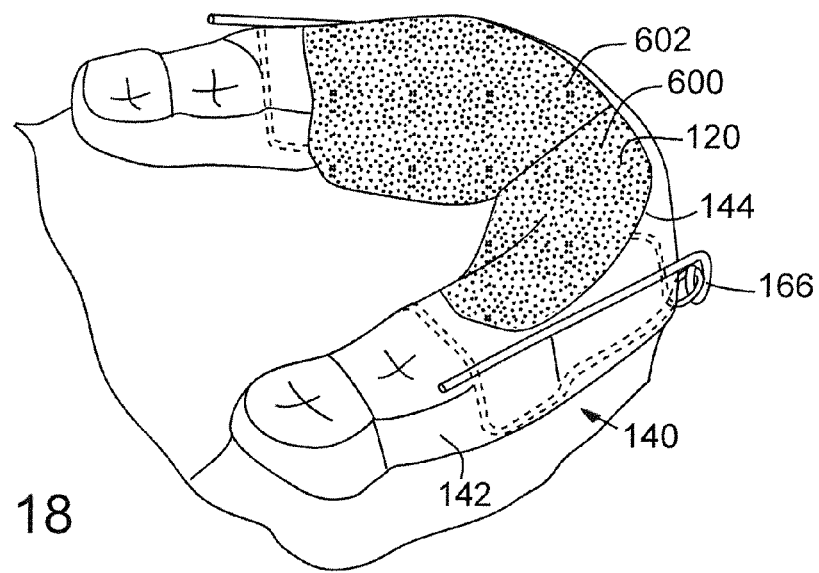
FIG. 18 is a perspective view of an exemplary lower jaw coupler and gripping surface support usable in the embodiment of FIG. 15.

FIGS. 15-19 illustrate a further embodiment of a tongue retainer. Components like those previously discussed have been assigned the same numbers and will not be discussed in detail. In the embodiment of these figures, the lower jaw coupler 142 is shown on the lower jaw of a user. The lower support 144 (FIG. 17) comprises a body having a gripping surface thereon with upwardly facing tongue gripping projections that some or all of which can be angled forwardly toward the tip of the tongue. As best seen in FIG. 18, the support 144 and projections can comprise first and second tongue gripping components 600, 602 that are positioned forwardly on the lower jaw coupler 142 in a generally U shaped configuration adjacent to the filiform papillae of the lower surface of the tongue for engaging the tongue when the tongue retainer is in position and the mouth is closed. The lower support 144 can be fixed to the lower jaw coupler with the lower jaw coupler mounted to the teeth of the user. Alternatively, a floating or pivoted lower jaw support 380, such as shown in FIG. 13A, can be used. In the example of FIGS. 15-19, the lower support 144 is desirably not tethered to the lower jaw coupler as it is fixed in place on the lower jaw coupler. The positioning of the tongue gripping elements 120 against the tongue when the apparatus is closed is shown in FIG. 17.

As can be seen in FIGS. 15 and 16, the illustrated tongue retainer can comprise tube and rod mechanisms 150, 152 for coupling the upper and lower jaw couplers together such as in the manner shown in FIG. 1. The upper jaw coupler 102 in this example comprises a palate plate 104 positioned to engage the upper palate of the user and interconnect the teeth engaging portions 102 of the upper jaw coupler. The dashed lines in FIG. 15 show reinforcing wires that can be embedded in the material that comprises the respective upper and lower jaw couplers.

Figure 19:
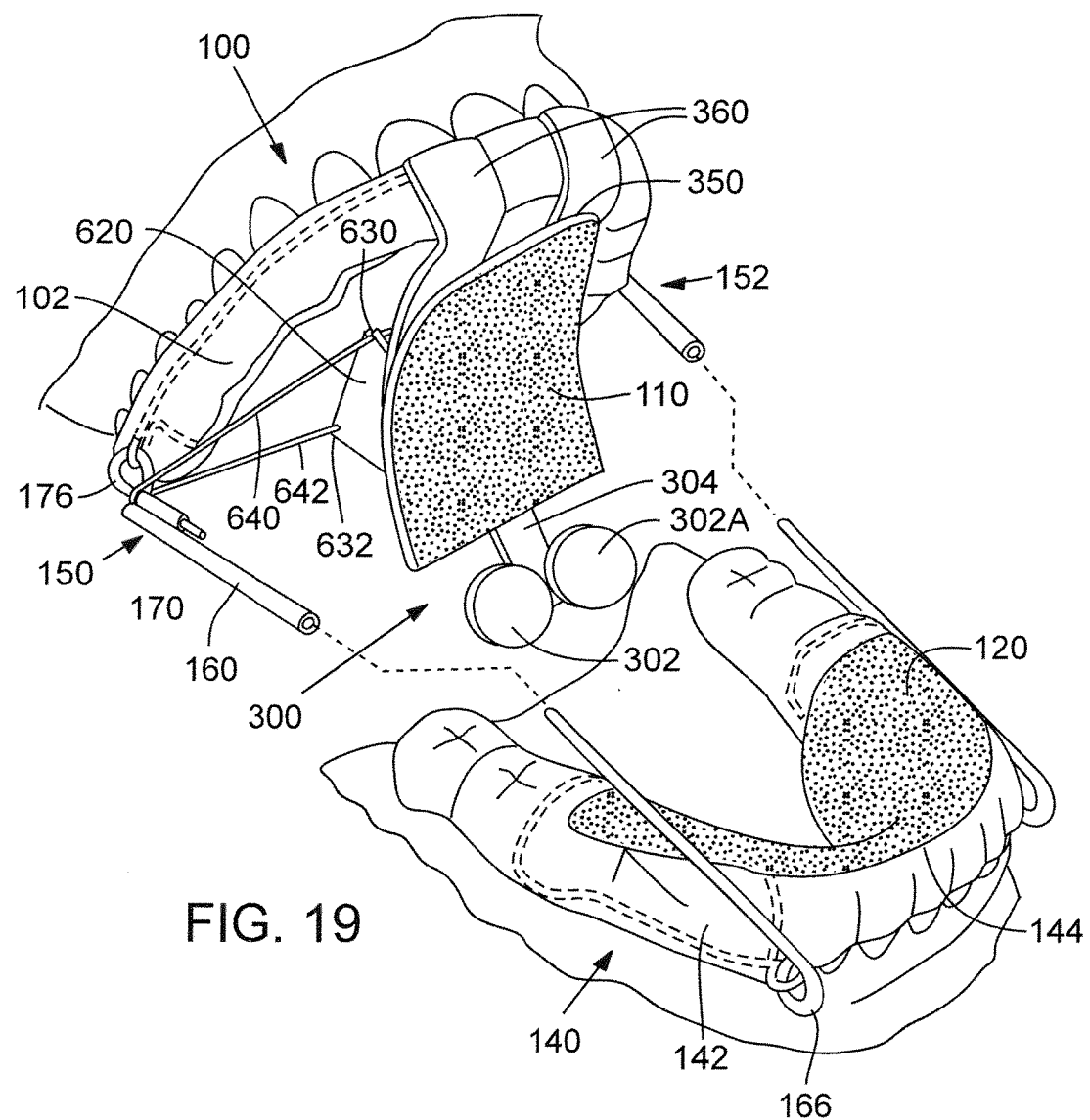
FIG. 19 is a perspective view of a tongue retainer of the form shown in FIG. 15 with the upper and lower components of the tongue retainer shown separated from one another for convenience in illustrating these components.

A rearwardly and downwardly extending tongue depressor assembly 300 is also shown in the embodiment of FIGS. 15-18, as is best seen in FIGS. 16, 17 and 19. The illustrated tongue depressor comprises an arm 304 having a distal end portion supporting first and second hemispherical or otherwise shaped tongue engagers 302, 302A. The arm 304 is slidably received through a channel provided in an arm receiving housing 310 mounted to the upper surface of the upper support 350 as best seen in FIG. 16. A projection 520 is also shown extending upwardly away from upper support 350 and more particularly in one example away from the upper surface thereof and toward the palate plate or palate engagement portion 104. A biasing member, that can comprise a single rubber band 610, engages the projection 520. The outer ends of the band 610 can be looped around outwardly projecting portions of the respective tube and rod mechanisms (e.g., portions 176) with the tube and rod mechanisms holding the outwardly positioned ends of the band in place. Thus, as can be seen in FIG. 16, the illustrated band 610 can extend from the tube and rod component 176 at a location along the rear buccal surface of the jaw coupler 102 at side 612 of the jaw coupler, across the lower biting surface at such side of the jaw coupler, into engagement with the projecting structure 520, across the biting surface of the jaw coupler 102 at the opposite side 614 of the jaw coupler, and into engagement with a component of the tube and rod mechanism, such as a projecting component 176 thereof, at the buccal side 614 of the jaw coupler. Thus, the band 610 is coupled to the respective sides of the jaw coupler at a rearward location of the jaw coupler in this example.

As can be seen in FIGS. 16 and 17, in one form the projecting structure 520 can comprise at least one plate and, in the illustrated example the structure comprises first and second plates 620, 622 that are spaced apart and interconnected by a reinforcing rib 624 extending between the plates. It should be noted that other forms of upwardly projecting structures can be used. With reference to FIG. 17, each of the plates include a first slot 630 opening generally upwardly and positioned along a front upper corner of the plate and a second slot 632 opening upwardly and positioned along a rear upper corner of the plate. A front portion of the band 640 (see FIG. 16) engages the front slots 630 and a rear portion 642 of the band engages the rear slots 632. As can be seen in FIG. 17, when the mouth is closed, the stretched bands have uppermost portions positioned above the bite plane of the biting surfaces of the upper jaw coupler to provide an enhanced downward force against the rear portion of the upper support to urge the tongue gripping surface 110 against the upper surface of the tongue. This also urges the tongue downwardly so that the gripping surface 120 of the lower support 144 grip the undersurface of the tongue. The tether 360 operates in the same manner as previously described in connection with FIGS. 13A-13E to allow movement of the upper support with the movement of the tongue. Also, with the mouth moved to a wide open position, the tongue retainer is operable like the retainer of FIG. 13E to facilitate the removal of the tongue retainer from the user's mouth. In the embodiment of FIGS. 15-19, desirably no biasing members interconnect the upper jaw coupler to the lower jaw coupler. In addition, desirably in this embodiment, the only biasing member comprises one or more downward force-applying members coupling a rear portion of the upper support to the respective sides of the upper jaw coupler. Thus, intra-arch biasing is desirably provided in this embodiment, with only the upper support being biased. Of course, additional biasing elements can be used in the embodiments of FIGS. 15-19, but this would be less desirable.

In the above description, various types of biasing mechanisms can be used, in addition to, in lieu of and/or in combination with springs and resilient materials such as elastic bands, to provide biasing forces to urge one or both of the upper and lower tongue gripping surfaces together. In addition, alternative manufacturing techniques can be used to provide tongue gripping surfaces. For example, in addition to approaches previously described, small spike-like tongue gripping projections can be made by hot stamping of a plastic panel or by using miniature round punches in a metal panel. In addition, for people with pierced tongues, the source of biasing between upper and lower tongue gripping surfaces can be a bolt or other mechanical fastener which engages upper and lower tongue gripping surfaces and extends through the pierced portion of the tongue.

Having illustrated and described the principles of my invention with reference to a number of embodiments, it should be apparent of those of ordinary skill in the art that these embodiments may be modified in arrangement in detail without departing from such principles. I claim all such embodiments and modifications that fall within a scope of any one or more of the following claims.

The invention claimed is:

1. An apparatus for grasping and restraining the tongue of a user, the apparatus comprising:

a first upper support;

the first upper support comprising an upper support body portion comprising an upper surface, a lower surface, a front, a rear, and first and second sides, the first upper support also comprising a first tongue gripping surface, the first tongue gripping surface comprising a plurality of tongue engaging projections that extend from the lower surface of the upper support body portion toward the upper surface of the front portion of the tongue of a user;

an upper jaw coupler comprising first and second side portions each with a buccal side and a lingual side, the first side portion being shaped to receive upper teeth of a user at a first side of the user's jaw and the second side portion being shaped to receive upper teeth of the user at a second side of the user's jaw opposite to the first side of the user's jaw to couple the first upper support to the upper jaw of the user, a pivot coupling the upper support body portion to the upper jaw coupler such that the front and rear of the upper support body portion is movable upwardly and downwardly relative to the upper jaw coupler and relative to the lower jaw of the user;

a second lower support;

the second lower support comprising a lower support body portion comprising an upper surface, a lower surface, a front, a rear, and first and second sides, the second lower support also comprising a second tongue gripping surface, the second tongue gripping surface comprising a plurality of tongue engaging projections that extend from the upper surface of the lower support body portion toward the lower surface of the front portion of the tongue of a user;

a lower jaw coupler adapted to couple the second lower support to the lower jaw of the user; and at least one biasing member coupled to the upper jaw coupler and to the first upper support and applying a biasing force to the first upper support to bias the movement of the first upper support and the first tongue gripping surface toward the second tongue gripping surface to grasp a front portion of a user's tongue positioned between the first and second tongue gripping surfaces so as to grasp and restrain the tongue of the user.

2. An apparatus according to claim 1 wherein the second lower support is fixed to the lower jaw coupler.

3. An apparatus according to claim 1 wherein the lower support body portion is pivotally coupled to the lower jaw coupler such that the lower support body portion is movable upwardly and downwardly relative to the lower jaw coupler.

4. An apparatus according to claim 1 wherein the pivot comprises a tether pivotally connecting the upper support body portion to the upper jaw coupler, the tether comprising first and second end portions, the first end portion of the tether being coupled to the front of the upper jaw coupler and the second end portion of the tether being connected to the first upper support at a location intermediate to the front and rear of the upper support body portion.

5. An apparatus according to claim 4 wherein the upper support body portion has a center, and wherein the second end portion of the tether is connected to the upper surface of the upper support body portion at a location that is at or rearwardly of the center of the upper support body portion and inwardly of the lingual sides of the first and second side portions of the upper jaw coupler.

6. An apparatus according to claim 4 wherein the tether is adjustable in length.

7. An apparatus according to claim 6 comprising a motor coupled to the tether and to the first upper support, the motor being operable to coil or uncoil the tether to adjust the length of the tether.

8. An apparatus according to claim 3 comprising a first tether pivotally connecting the upper support body portion to a front portion of the upper jaw coupler, wherein the first tether is connected to the upper surface of the upper support body portion at a location that is rearwardly of a central portion of the upper support body portion, and a second tether pivotally connecting the front of the lower support body portion to the lower jaw coupler.

9. An apparatus according to claim 8 wherein the first and second tethers are each adjustable in length.

10. An apparatus according to claim 1 comprising first and second telescoping mechanisms positioned along respective sides of the upper and lower jaw couplers, each of the first and second telescoping mechanisms comprising first and second end portions, the first end portion being coupled to the upper jaw coupler and the second end portion being coupled to the lower jaw coupler.

11. An apparatus according to claim 10 wherein each of the first and second telescoping mechanisms comprises a tube and rod mechanism having a length and comprising a first sleeve portion having a rod receiving bore, a rod slidably received by the rod receiving bore, a second threaded sleeve portion coupled to the first sleeve portion and a threaded support coupler threaded into the second threaded sleeve portion, wherein rotation of the threaded support coupler in a first direction shifts the threaded support coupler into the second threaded sleeve portion and rotation of the threaded support coupler in a second direction shifts the threaded support coupler out of the second threaded sleeve portion to thereby adjust the length of the rod and tube mechanism, wherein the first sleeve portion comprises at least one first anti-rotation surface within the rod receiving bore and the rod comprises at least one second anti-rotation surface, the first and second anti-rotation surfaces engaging one another to prevent rotation of the rod relative to the first sleeve portion.

12. An apparatus according to claim 1 wherein the at least one biasing member is coupled to the upper jaw coupler and is also coupled to the upper surface of the upper support body portion to apply a biasing force to the upper surface of the upper support body portion so as to move the first upper support downwardly relative to the upper jaw coupler toward the second lower support at least when the user's mouth is closed.

13. An apparatus according to claim 1 wherein the upper jaw coupler comprises first and second side portions each with a buccal side and a lingual side and with a downwardly facing upper coupler biting surface, the upper support body portion having an upper surface and being positioned inwardly of the lingual sides of the first and second side portions, the at least one biasing member extending from a rear portion of the buccal side of the first side portion of the upper jaw coupler, across the downwardly facing upper coupler biting surface of the first side portion of the upper jaw coupler<<,>>across the upper surface of the upper support body portion, across the downwardly facing upper coupler biting surface of the second side portion of the upper jaw coupler and to a rear portion of the buccal side of the second side portion of the upper jaw coupler, the at least one biasing member exerting a downward force on the upper surface of the upper support body portion at least when the user's mouth is in a closed position.

14. An apparatus according to claim 13 wherein the upper support body portion comprises an upwardly extending biasing member engaging projection that is positioned inwardly of the lingual sides of the first and second side portions and engaged by the biasing member to exert the downward force.

15. An apparatus according to claim 14 wherein the biasing member engaging projection comprises at least one elongated projection extending from a front portion of the upper support toward a rear portion of the upper support, the at least one biasing member engaging the at least one elongated projection at an upper front portion and at an upper rear portion of the at least one elongated projection.

16. An apparatus according to claim 15 wherein the at least one elongated projection comprises at least one plate.

17. An apparatus according to claim 16 wherein the at least one plate comprises a front portion with a first upwardly opening slot having a first band receiving opening and a rear portion with a second upwardly opening slot having a second band receiving opening, the at least one biasing member comprising at least one elastic band positioned in the first upwardly opening slot and at least one elastic band positioned in the second upwardly opening slot.

18. An apparatus according to claim 13 wherein the at least one biasing member comprises an elastic band.

19. An apparatus according to claim 1 comprising a tongue depressor coupled to the upper support body portion and projecting rearwardly and downwardly from the upper support body portion for engaging an upper surface of the rear portion of the user's tongue.

20. An apparatus according to claim 19 wherein the tongue depressor is movable relative to the upper support body portion in front to rear directions, rear to front directions, and upward and downward directions.

21. An apparatus according to claim 19 wherein the tongue depressor comprises an elongated arm comprising a first end portion slidably coupled to the upper support body portion and a second distal end portion and a tongue engager mounted to the second distal end portion, the elongated arm being slidable to a position at which the tongue engager is positioned rearwardly of the upper jaw coupler and downwardly below the lower surface of the upper jaw coupler.

22. An apparatus according to claim 19 wherein the tongue depressor comprises at least one elongated arm with a first arm portion coupled to the upper support body portion and a second distal arm end portion spaced rearwardly from the upper support body portion, and a tongue engager, wherein the tongue engager comprises first and second tongue engaging elements offset from the center of the at least one elongated arm.

23. An apparatus according to claim 21 wherein the elongated arm comprises a bendable material that retains a position to which it is bent, wherein bending the elongated arm downwardly relative to the upper support body portion shifts and positions the tongue engager downwardly relative to the rear of the upper support body portion and bending the elongated arm upwardly relative to the upper support body portion shifts and positions the tongue engager upwardly relative to the rear of the upper support body portion.

24. An apparatus according to claim 19 wherein the tongue depressor comprises at least one elongated arm threadedly coupled to the upper support body portion and extending in a front to rear direction, the at least one elongated arm comprising a distal end portion spaced from the upper support body portion, an enlarged tongue engager mounted to the distal end portion of the at least one elongated arm, wherein rotation of the at least one elongated arm in a first direction shifts the at least one elongated arm and enlarged tongue engager axially relative to the upper support body portion in a rearward direction and rotation of the at least one elongated arm in a second direction opposite to the first direction shifts the at least one elongated arm and enlarged tongue engager axially relative to the upper support body portion in a forward direction.

25. An apparatus according to claim 24 comprising an arm support operatively coupled to the upper surface of the upper support body portion for raising and lowering relative to the upper surface of the upper support body portion, a first portion of the at least one elongated arm being carried by the arm support, a pivot mounted to the upper support body portion at a location spaced rearwardly of the arm support, the pivot pivotally coupling the at least one elongated arm to the upper support body portion, wherein raising of the arm support relative to the upper support body portion raises the first portion of the at least one elongated arm and pivots the distal end of the at least one elongated arm and the enlarged tongue engager downwardly about the pivot and lowering the arm support relative to the upper support body portion lowers the first portion of the at least one elongated arm and pivots the distal end of the at least one elongated arm and the enlarged tongue engager upwardly about the pivot.

26. An apparatus for grasping and restraining the front portion of the tongue of a user, the apparatus comprising:
   a first upper support;
   the first upper support comprising a first tongue gripping surface, the first tongue gripping surface comprising a plurality of tongue engaging projections that extend toward the upper surface of a front portion of the tongue of a user;
   an upper jaw coupler adapted to couple the first upper support to the upper jaw of the user;
   a second lower support;
   the second lower support comprising a second tongue gripping surface, the second tongue gripping surface comprising a plurality of tongue engaging projections that extend toward the lower surface of a front portion of the tongue of a user;
   a lower jaw coupler adapted to couple the second lower support to the lower jaw of the user;
   at least one biasing member coupled to the first upper support and biasing the first gripping surface toward the second tongue gripping surface to grasp a portion of a front portion of a user's tongue positioned between the first and second tongue gripping surfaces so as to grasp and restrain the front portion of the tongue of the user; and
   a tongue depressor comprising an elongated arm comprising a first arm end portion coupled to the upper support body portion and a second distal arm end portion and a tongue engager mounted to the second distal arm end portion, the second distal arm end portion supporting the tongue engager at a location positioned rearwardly of and downwardly from the upper support body portion.

27. An apparatus according to claim 26 wherein the tongue depressor is movable relative to the first upper support in a front to rear direction, in a rear to front direction, and in upward and downward directions.

28. An apparatus according to claim 27 wherein the tongue depressor is slidably coupled to the first upper support.

29. An apparatus according to claim 27 wherein the tongue depressor comprises a tongue engager comprising first and second tongue engaging elements supported by the second distal arm end portion on opposite sides of the center of the second distal arm end portion.

30. An apparatus according to claim 29 wherein the elongated arm comprises a bendable material, wherein bending the elongated arm downwardly relative to the first upper support shifts the tongue engager downwardly and bending the elongated arm upwardly relative to the upper support shifts the tongue engager upwardly.

31. An apparatus according to claim 27 wherein the tongue depressor comprises at least one elongated arm threadedly coupled to the first upper support and extending in a front to rear direction, the at least one elongated arm comprising a distal end portion spaced from the first upper support and extending rearwardly and downwardly from the first upper support, and an enlarged tongue engager mounted to the distal end portion of the at least one elongated arm, wherein rotation of the at least one elongated arm in a first direction shifts the at least one elongated arm and enlarged tongue engager axially relative to the first upper support in a rearward and downward direction and rotation of the at least one elongated arm in a second direction opposite to the first direction shifts the at least one elongated arm and enlarged tongue engager axially relative to the first upper support in a forward and upward direction.

32. An apparatus according to claim 31 comprising an arm support operatively coupled to the first upper support for raising and lowering relative to the first upper support, a first portion of the at least one elongated arm being carried by the arm support, a pivot mounted to the first upper support at a location spaced rearwardly of the arm support, the pivot pivotally coupling the at least one elongated arm to the first upper support, wherein raising of the arm support relative to the first upper support raises the first portion of the at least one elongated arm and pivots the distal end of the at least one elongated arm and the enlarged tongue engager downwardly about the pivot and lowering of the arm support relative to the first upper support lowers the first portion of the at least one elongated arm and pivots the distal end of the at least one elongated arm and the enlarged tongue engager upwardly about the pivot.

33. An upper jaw assembly for an apparatus for grasping and restraining the tongue of a user, the user having an upper jaw with first and second jaw sides with upper teeth projecting from the upper jaw, the assembly comprising:

a first upper support;

the first upper support comprising an upper support body portion comprising an upper surface, a lower surface, a front, a rear, and first and second sides, the first upper support also comprising a first tongue gripping surface, the first tongue gripping surface comprising a plurality of tongue engaging projections that extend from the lower surface of the upper support body portion that are angled toward the upper surface of the front portion of the tongue of a user; and an upper jaw coupler comprising first and second side portions each with a buccal side and a lingual side, the first side portion being shaped to receive at least some of the upper teeth of a user along the first jaw side and the second side portion being shaped to receive at least some of the upper teeth of a user along the second jaw side, a pivot comprising first and second pivot end portions, the first pivot end portion coupled to the upper jaw coupler and the second pivot end portion coupled to the upper support body portion at a location inwardly of the lingual sides of the first and second side portions, the pivot coupling the upper support body portion to the upper jaw coupler such that the front and rear of the upper support body portion is movable upwardly and downwardly relative to the upper jaw coupler.

34. An apparatus according to claim 33 comprising a tongue depressor coupled to the upper support body portion and projecting rearwardly and downwardly from the upper support body portion for engaging a rear portion of the upper surface of a user's tongue.

35. An apparatus according to claim 34 wherein the tongue depressor is movable relative to the upper support body portion in front to rear directions and rear to front directions and upward and downward directions.

36. An apparatus according to claim 35 wherein the tongue depressor comprises a tongue engager and wherein the tongue depressor is slidably coupled to the first upper support and is slidable to a position which positions the tongue engager rearwardly of the rear most upper teeth of a user of the apparatus and downwardly below the lower surface of the rearward teeth of the user of the apparatus.

37. An apparatus according to claim 34 wherein the upper jaw coupler comprises a front portion, wherein the pivot comprises a tether pivotally connecting the upper support body portion to the front portion of the upper jaw coupler, the tether being connected to the first upper support at a location intermediate to the front and rear of the upper support body portion.

38. An apparatus according to claim 33 wherein the upper jaw coupler comprises first and second side portions each with a buccal side and a lingual side, and the upper support body portion has a center, and wherein the second pivot end portion of the povit is connected to the upper surface of the upper support body portion at a location that is at or rearwardly of the center of the upper support body portion and inwardly of the lingual sides of the first and second side portions of the upper jaw coupler.

* * * * *

UNITED STATES PATENT AND TRADEMARK OFFICE
CERTIFICATE OF CORRECTION

PATENT NO.         : 9,801,755 B2
APPLICATION NO.    : 13/310601
DATED              : October 31, 2017
INVENTOR(S)        : John D. Summer It is certified that error appears in the above-identified patent and that said Letters Patent is hereby corrected as shown below:

In the Claims

Claim 13, Column 28, Line 63, "jaw coupler<<,>>across the upper surface of the upper" should read --jaw coupler, across the upper surface of the upper--.

Signed and Sealed this
Twenty-eighth Day of May, 2019

Andrei Iancu
*Director of the United States Patent and Trademark Office*